(12) United States Patent
Pan et al.

(10) Patent No.: US 10,323,180 B2
(45) Date of Patent: Jun. 18, 2019

(54) DEUTERATED ORGANIC COMPOUND, MIXTURE AND COMPOSITION CONTAINING SAID COMPOUND, AND ORGANIC ELECTRONIC DEVICE

(71) Applicant: GUANGZHOU CHINARAY OPTOELECTRONIC MATERIALS LTD., Guangzhou, Guangdong (CN)

(72) Inventors: Junyou Pan, Guangdong (CN); Xiaolin Yan, Guangdong (CN); Hong Huang, Guangdong (CN)

(73) Assignee: GUANGZHOU CHINARAY OPTOELECTRONIC MATERIALS LTD., Guangzhou, Guangdong (CN)

( * ) Notice: Subject to any disclaimer, the term of this patent is extended or adjusted under 35 U.S.C. 154(b) by 39 days.

(21) Appl. No.: 15/532,876

(22) PCT Filed: Dec. 3, 2015

(86) PCT No.: PCT/CN2015/096327
§ 371 (c)(1),
(2) Date: Sep. 8, 2017

(87) PCT Pub. No.: WO2016/086885
PCT Pub. Date: Jun. 9, 2016

(65) Prior Publication Data
US 2018/0010040 A1    Jan. 11, 2018

(30) Foreign Application Priority Data

Dec. 4, 2014    (CN) .......................... 2014 1 0730178

(51) Int. Cl.
| | | |
|---|---|---|
| *C07B 59/00* | (2006.01) | |
| *C09K 11/06* | (2006.01) | |
| *C07C 255/58* | (2006.01) | |
| *C07D 221/20* | (2006.01) | |
| *C07D 403/10* | (2006.01) | |
| *C07D 403/14* | (2006.01) | |

(Continued)

(52) U.S. Cl.
CPC ............ *C09K 11/06* (2013.01); *C07B 59/002* (2013.01); *C07C 255/58* (2013.01); *C07D 209/08* (2013.01); *C07D 209/10* (2013.01); *C07D 209/86* (2013.01); *C07D 209/88* (2013.01); *C07D 221/20* (2013.01); *C07D 403/10* (2013.01); *C07D 403/14* (2013.01); *C07D 413/10* (2013.01); *C07D 487/04* (2013.01); *C07D 487/16* (2013.01); *C07D 519/00* (2013.01); *H01L 51/0052* (2013.01); *H01L 51/0059* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0094* (2013.01); *C07B 2200/05* (2013.01); *C07C 2603/94* (2017.05); *C09K 2211/1007* (2013.01); *C09K 2211/1014* (2013.01); *C09K 2211/1018* (2013.01); *C09K 2211/1029* (2013.01); *C09K 2211/1033* (2013.01); *C09K 2211/1059* (2013.01); *C09K 2211/1074* (2013.01); *H01L 51/5012* (2013.01)

(58) Field of Classification Search
CPC ..................................................... C07D 219/02
USPC .......................................................... 257/40
See application file for complete search history.

(56) References Cited

U.S. PATENT DOCUMENTS

| | | |
|---|---|---|
| 3,567,450 A | 3/1971 | Brantley et al. |
| 3,615,404 A | 10/1971 | Price et al. |

(Continued)

FOREIGN PATENT DOCUMENTS

| | | |
|---|---|---|
| CN | 1583691 | 2/2005 |
| CN | 101521264 | 9/2009 |

(Continued)

OTHER PUBLICATIONS

C. Adachi et al., "High-efficiency red electrophosphorescence devices," Applied Physics Letters, vol. 78, No. 11 (2001), p. 1622-1624.

(Continued)

*Primary Examiner* — Khanh T Nguyen
(74) *Attorney, Agent, or Firm* — Hamre, Schumann, Mueller & Larson, P.C.

(57) ABSTRACT

The present disclosure discloses a deuterated organic compound and a formulation and an organic electronic device containing the same, wherein the deuterated organic compound has the following structural formula:

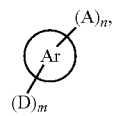

wherein Ar is an aromatic or heteroaromatic structural unit, D is an electron donor group, A is an electron acceptor group, n and m are an integer between 1 and 6; and wherein for the organic compound, (S1−T1)≤0.25 eV, and at least one H atom of the organic compound is substituted by deuterium. The present disclosure achieves the improvement of the electroluminescence quantum efficiency and the lifetime of the organic compound by replacing the H atom in the organic compound with deuterium and having (S1−T1) ≤0.35 eV, and the material of the present disclosure has a great application potential and application range due to its low cost and relatively simple synthesis process.

17 Claims, No Drawings

(51) Int. Cl.
  *C07D 487/04* (2006.01)
  *C07D 487/16* (2006.01)
  *C07D 519/00* (2006.01)
  *C07D 209/86* (2006.01)
  *C07D 209/88* (2006.01)
  *H01L 51/00* (2006.01)
  *C07D 413/10* (2006.01)
  *C07D 209/08* (2006.01)
  *C07D 209/10* (2006.01)
  *H01L 51/50* (2006.01)

(56) References Cited

U.S. PATENT DOCUMENTS

| | | | |
|---|---|---|---|
| 4,720,432 | A | 1/1988 | VanSlyke et al. |
| 4,769,292 | A | 9/1988 | Tang et al. |
| 5,061,569 | A | 10/1991 | VanSlyke et al. |
| 5,121,029 | A | 6/1992 | Hosokawa et al. |
| 5,130,603 | A | 7/1992 | Tokailin et al. |
| 6,020,078 | A | 2/2000 | Chen et al. |
| 6,251,531 | B1 | 6/2001 | Enokida et al. |
| 6,824,895 | B1 | 11/2004 | Sowinski et al. |
| 6,830,828 | B2 | 12/2004 | Thompson et al. |
| 6,835,469 | B2 | 12/2004 | Kwong et al. |
| 7,029,766 | B2 | 4/2006 | Huo et al. |
| 7,250,226 | B2 | 7/2007 | Tokito et al. |
| 7,250,532 | B2 | 7/2007 | Iwakuma et al. |
| 7,767,317 | B2 | 8/2010 | Begley et al. |
| 2001/0053462 | A1 | 12/2001 | Mishima |
| 2003/0091862 | A1 | 5/2003 | Tokito et al. |
| 2004/0002576 | A1 | 1/2004 | Oguma et al. |
| 2004/0076853 | A1 | 4/2004 | Jarikov |
| 2005/0258742 | A1 | 11/2005 | Tsai et al. |
| 2006/0210830 | A1 | 9/2006 | Funahashi et al. |
| 2006/0222886 | A1 | 10/2006 | Kwong et al. |
| 2007/0087219 | A1 | 4/2007 | Ren et al. |
| 2007/0205714 | A1 | 9/2007 | Busing et al. |
| 2007/0208567 | A1 | 9/2007 | Amento et al. |
| 2007/0252517 | A1 | 11/2007 | Owczarczyk et al. |
| 2008/0027220 | A1 | 1/2008 | Stossel et al. |
| 2008/0113101 | A1 | 5/2008 | Inoue et al. |
| 2009/0061681 | A1 | 3/2009 | McMunigal et al. |
| 2009/0134784 | A1 | 5/2009 | Lin et al. |
| 2009/0218938 | A1 | 9/2009 | Takeda et al. |
| 2011/0284799 | A1 | 11/2011 | Stossel et al. |
| 2012/0056170 | A1 | 3/2012 | Pan et al. |
| 2012/0061617 | A1 | 3/2012 | Heun et al. |
| 2016/0072076 | A1* | 3/2016 | Stoessel .............. C07D 219/02 257/40 |

FOREIGN PATENT DOCUMENTS

| | | |
|---|---|---|
| CN | 102282150 | 12/2011 |
| CN | 103467450 | 12/2013 |
| DE | 102004020298 | 11/2005 |
| DE | 102005058557 | 6/2007 |
| DE | 102009023156 | 12/2010 |
| DE | 102009023154 | 6/2011 |
| EP | 1144543 | 3/2004 |
| EP | 1191613 | 3/2006 |
| EP | 1191614 | 5/2009 |
| EP | 1191612 | 9/2009 |
| EP | 1941562 | 5/2010 |
| EP | 1957606 | 11/2017 |
| JP | 2913116 | 6/1999 |
| JP | 2003338375 | 11/2003 |
| JP | 2005108556 | 4/2005 |
| JP | 2005285661 | 10/2005 |
| JP | 2007059939 | 3/2007 |
| JP | 2007197574 | 8/2007 |
| JP | 2007211243 | 8/2007 |
| JP | 2008053397 | 3/2008 |
| WO | 00/70655 | 11/2000 |
| WO | 01/21729 | 3/2001 |
| WO | 01/41512 | 6/2001 |
| WO | 02/02714 | 1/2002 |
| WO | 02/15645 | 2/2002 |
| WO | 03/020790 | 3/2003 |
| WO | 03/051092 | 6/2003 |
| WO | 03/099901 | 12/2003 |
| WO | 2004/041901 | 5/2004 |
| WO | 2004/113412 | 12/2004 |
| WO | 2005/019373 | 3/2005 |
| WO | 2005/033174 | 4/2005 |
| WO | 2005/033244 | 4/2005 |
| WO | 2005/056633 | 6/2005 |
| WO | 2005/104264 | 11/2005 |
| WO | 2006/000388 | 1/2006 |
| WO | 2006/000389 | 1/2006 |
| WO | 2006/052457 | 5/2006 |
| WO | 2006/058737 | 6/2006 |
| WO | 2006/062226 | 6/2006 |
| WO | 2006/114364 | 11/2006 |
| WO | 2006/118345 | 11/2006 |
| WO | 2006/122630 | 11/2006 |
| WO | 2007/043495 | 4/2007 |
| WO | 2007/065549 | 6/2007 |
| WO | 2007/095118 | 8/2007 |
| WO | 2007/115610 | 10/2007 |
| WO | 2007/140847 | 12/2007 |
| WO | 2008/006449 | 1/2008 |
| WO | 2009/118087 | 10/2009 |
| WO | 2009/146770 | 12/2009 |
| WO | 2010/015307 | 2/2010 |
| WO | 2010/031485 | 3/2010 |
| WO | 2010/054728 | 5/2010 |
| WO | 2010/054731 | 5/2010 |
| WO | 2010/086089 | 8/2010 |
| WO | 2010/099852 | 9/2010 |
| WO | 2010/102709 | 9/2010 |
| WO | 2010/135519 | 11/2010 |
| WO | 2011/110277 | 9/2011 |
| WO | 2011/141110 | 11/2011 |
| WO | 2011/157339 | 12/2011 |
| WO | 2012/004407 | 1/2012 |
| WO | 2012/007086 | 1/2012 |
| WO | 2012/007087 | 1/2012 |
| WO | 2012/007088 | 1/2012 |
| WO | 2014/146752 | 9/2014 |
| WO | WO 2014-146752 A1 * 9/2014 ........... C07D 209/82 |

OTHER PUBLICATIONS

M. A. Baldo et al., "High-efficiency fluorescent organic light-emitting devices using a phosphorescent sensitizer," Nature, vol. 403 (2000), p. 750-753.

V. Bulovic et al., "Transparent light-emitting devices," Nature, vol. 380 (1996), p. 29.

K. Goushi et al., "Organic light-emitting diodes employing efficient reverse intersystem crossing for triplet-to-singlet state conversion," Nature Photonics, vol. 6 (2012), p. 253-258.

G. Gu et al., "Transparent organic light emitting devices," Appl. Phys. Lett., vol. 68, No. 19 (1996), p. 2606-2608.

C. E. Johnson et al., "Luminescent Iridium(I), Rhodium(I), and Platinum(II) Dithiolate Complexes," J. Am. Chem. Soc., vol. 105 (1983), p. 1795-1802.

J. Kido et al., "Bright red light-emitting organic electroluminescent devices having a europium complex as an emitter," Appl. Phys. Lett., vol. 65 (1994), p. 2124-2126.

J. Kido et al., "Electroluminescence in a Terbium Complex" Chemistry Letters (1990), p. 657-660.

H. Kipphan, Excerpt of "Handbook of Print Media," Springer-Verlag Berlin Heidelberg, (2001) 13 pages.

Y. Ma et al., "Electroluminescence from triplet metal-ligand charge-transfer excited state of transition metal complexes," Synthetic Metals, vol. 94 (1998), p. 245-248.

H. Uoyama et al., "Highly efficient organic light-emitting diodes from delayed fluorescence," Nature, vol. 492 (2012), p. 234-238.

M. Wrighton and D.L. Morse, "The Nature of the Lowest Excited State in Tricarbonylchloro-1,10-phenanthrolinerhenium(I) and Related

(56) References Cited

OTHER PUBLICATIONS

Complexes," Journal of the American Chemical Society, vol. 96, No. 4 (1974), p. 998-1003.
G. R. Newkome et al., "Dendrimers and Dendrons: Concepts, Syntheses, Applications," Wiley-VCH, ISBN: 3527299971, 2002 (320 pages).
International Search Report for international appl. No. PCT/CN2015/096327, dated Mar. 15, 2016 (2 pages).
F. Faigl et al., "The Special Directing Effect of Fluorine: Ligand Independent Ortho Lithiation of 1-(fluorophenyl) pyrroles," Tetrahedron, vol. 54 (1998), p. 4367-4374.

\* cited by examiner

DEUTERATED ORGANIC COMPOUND, MIXTURE AND COMPOSITION CONTAINING SAID COMPOUND, AND ORGANIC ELECTRONIC DEVICE

TECHNICAL FIELD

The present disclosure relates to the field of organic materials, and more particularly to a deuterated organic compound and a mixture, a formulation and an organic electronic device containing the same.

BACKGROUND

Organic light-emitting diodes (OLEDs) made of organic semiconductor materials have a great potential in the applications of novel optoelectronic devices such as in the applications of flat panel displays and lighting because of the synthetic diversity, low manufacturing cost, and high optical and electrical performance of organic semiconductive materials, making it possible to manufacture a large-scale flexible device. In order to improve the luminous efficiency of organic light-emitting diodes, various light emitter materials based on fluorescence and phosphorescence have been developed. The organic light-emitting diode of the fluorescent material has a high reliability; however, since the branching ratio of the singlet excited state and the triplet excited state of an exciton is 1:3, its internal electroluminescence quantum efficiency is limited to 25% under the electrical excitation. In contrast, the internal luminescence quantum efficiency of organic light-emitting diodes using phosphorescent materials has achieved almost 100%. So far, the phosphorescent materials which have practical value are iridium and platinum complexes; the cost is quite high since the raw material is rare and expensive and the synthesis of the complex is rather complicated.

In order to solve this problem, Adachi proposed the concept of reverse intersystem crossing so that an organic compound can be used, i.e. without using the metal complex, to achieve a high efficiency of phosphorescent OLED. Such a concept has come true by 1) an exciplex, see Adachi et al., Nature Photonics, Vol 6, p253 (2012); 2) thermal excited delayed fluorescent material TADF, see Adachi et al., Nature Vol 492, 234 (2012). But the OLED devices still have a very short life.

Obviously the efficiency and the life of the existing luminescent materials have yet to be improved.

Therefore, there is a need for improvement and development of the existing technology.

SUMMARY OF THE INVENTION

In view of the above-mentioned deficiencies of the prior art, it is an object of the present disclosure to provide a deuterated organic compound and a mixture, a formulation and an organic electronic device containing the same, aiming to solve the problem that the existing luminescent materials still need to improve their efficiency and life.

The present disclosure provides an organic compound having the following structural formula (I):

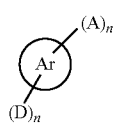

(I)

wherein Ar may be an aromatic or heteroaromatic structural unit, n and m may be an integer between 1 and 6, D may be an electron donor group, wherein when m>1, each D may be independently selected from the same or different electron donor groups, A may be an electron acceptor group, wherein when n>1, each A may be independently selected from the same or different electron acceptor groups; and wherein for the organic compound, (S1−T1)≤0.35 eV and at least one H atom of the organic compound may be substituted by deuterium.

Preferably, the organic compound has (S1−T1)≤0.25 eV.

In a preferred embodiment, in the organic compound, at least one H atom in at least one electron donor group D may be substituted by deuterium.

In another preferable embodiment, in the organic compound, at least one H atom in at least one electron acceptor group A may be substituted by deuterium.

In some embodiments, in the organic compound, at least one H atom in Ar may be substituted by deuterium.

In a preferred embodiment, in the deuterated organic compound, more than 20%, preferably more than 30%, more preferably more than 40%, and most preferably more than 50% of the H atoms may be substituted by deuterium.

In a preferred embodiment, in the deuterated organic compound, the electron donor group D may contain any of the following groups:

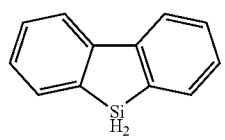
D1

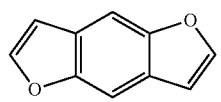
D2

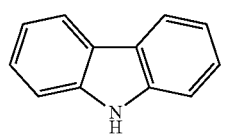
D3

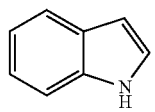
D4

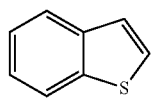
D5

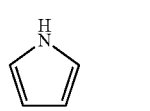
D6

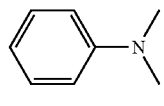
D7

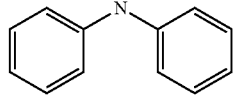
D8

-continued

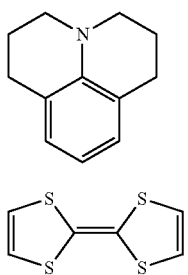

In a preferred embodiment, in the deuterated organic compound, the electron acceptor group A may be selected from F, cyano group, and groups containing any of the following:

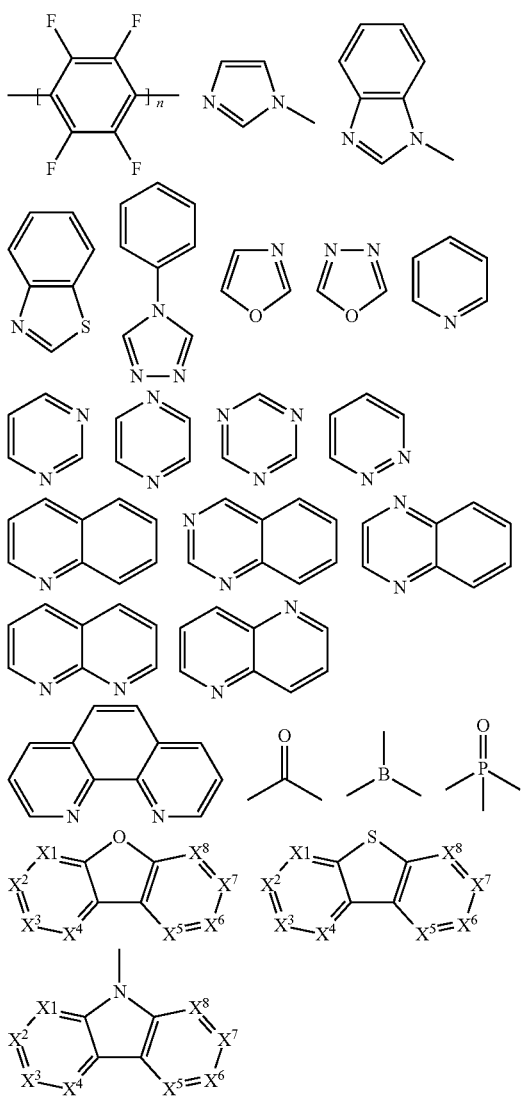

wherein n may be an integer between 1 to 3, $X^1$-$X^8$ may be selected from $CR^1$ or N, and at least one of $X^1$-$X^8$ is N, and wherein $R^1$ may be selected from any of the following groups: hydrogen, alkyl, alkoxy, amino, alkenyl, alkynyl, aralkyl, heteroalkyl, aryl, and heteroaryl.

In a preferred embodiment, in the deuterated organic compound, Ar may be selected from any of the following groups:

wherein z may be O or S.

In a preferred embodiment, in the deuterated organic compound, more than 20%, preferably more than 30%, more preferably more than 40%, and most preferably more than 50% of the H atoms may be substituted by deuterium.

The present disclosure further provides a deuterated mixture containing at least one organic compound as described above and further containing an organic functional material selected from a hole (also called an electron hole)-injection or hole-transport material (HIM/HTM), a hole-blocking material (HBM), an electron-injection or electron-transport material (EIM/ETM), an electron-blocking material (EBM), an organic host material (Host), a singlet emitter (fluorescent emitter), and a triplet emitter (phosphorescent emitter).

The present disclosure further relates to a formulation containing the organic compound or the mixture as described above, and at least one organic solvent. The present disclosure further provides a film prepared in a solution and containing the compound according to the present disclosure.

The present disclosure further relates to an organic electronic device containing the organic compound as described above.

The organic electronic device is selected from organic light emitting diode (OLED), organic photovoltaic cell (OPV), organic light emitting electrochemical cell (OLEEC), organic field effect transistor (OFET), organic light emitting field effect transistor, organic laser, organic spintronic device, organic sensor, and organic plasmonic emitter diode.

Advantageous effects: the present disclosure achieves the improvement of the internal electroluminescence quantum efficiency and the lifetime of the organic compound by replacing the H atom in the organic compound with deuterium and having (S1–T1)≤0.35 eV, and the material of the present disclosure has a great application potential and application range due to its low cost and relatively simple synthesis process.

DETAILED EMBODIMENTS OF THE INVENTION

The present disclosure provides a deuterated organic compound and a mixture, a formulation and an organic electronic device containing the same. The present disclosure will now be described in greater detail with reference to the accompanying drawings so that the purpose, technical solutions, and technical effects thereof are more clear and comprehensible. It is to be understood that the specific embodiments described herein are merely illustrative of, and are not intended to limit, the disclosure.

The present disclosure provides an organic compound having the following structural formula (I):

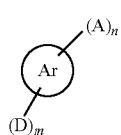 (I)

wherein Ar may be an aromatic or heteroaromatic structural unit, n and m are an integer between 1 and 6, D may be an electron donor group, wherein when m>1, each D may be independently selected from the same or different electron donor groups, A may be an electron acceptor group, wherein when n>1, each A may be independently selected from the same or different electron acceptor groups; and wherein for the organic compound, (S1−T1)≤0.35 eV and at least one H atom of the organic compound is substituted by deuterium.

"(S1−T1)" refers to an energy difference between the S1 state and the T1 state of an organic compound, which can be determined by spectral measurement or analogously calculated as described below.

The organic compound according to the present disclosure is a small molecular material.

As used herein, the term "small molecule" refers to a molecule that is not a polymer, oligomer, dendrimer, or blend. In particular, there is no repetitive structure in small molecules. The molecular weight of the small molecule is no greater than 3000 g/mole, more preferably no greater than 2000 g/mole, and most preferably no greater than 1500 g/mole.

Polymer includes homopolymer, copolymer, and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

Conjugated polymer is a polymer whose backbone is primarily consisted of the sp2 hybrid orbital of carbon (C) atom. Some known examples are polyacetylene and poly(phenylene vinylene), on the backbone of which the C atom can also be optionally substituted by other non-C atoms, and which is still considered to be a conjugated polymer when the sp2 hybridization on the backbone is interrupted by some natural defects. In addition, the conjugated polymer in the present disclosure may also comprise aryl amine, aryl phosphine and other heteroaromatics, organometallic complexes, and the like on the backbone.

According to a first aspect of the present disclosure, at least one H atom of the organic compound is substituted by deuterium.

The present disclosure shows that the compound after deuteration has a good stability, and the OLED containing the compound after deuteration has a longer lifetime. The possible mechanism is, but is not limited to, the reaction rate of the C—H bond is usually 6 to 10 times faster than that of the corresponding C-D bond due to the kinetic isotope effect. Therefore, when the OLED is working, the compound containing the compound after deuteration has a relatively slow decay in the kinetic process of the decay.

In some embodiments, those H with a higher reactivity are substituted by deuterium.

In a preferred embodiment, in the organic compound, at least one H atom in at least one electron donor group D is substituted by deuterium.

In another preferable embodiment, in the organic compound, at least one H atom in at least one electron acceptor group A is substituted by deuterium.

In some embodiments, in the organic compound, at least one H atom in Ar is substituted by deuterium.

In a preferred embodiment, in the organic compound, more than 20%, preferably more than 30%, more preferably more than 40%, and most preferably more than 50% of the H atoms are substituted by deuterium.

In nature, the abundance of deuterium in the ocean is 0.0156%; that is, there is one deuterium among 6420 hydrogen atoms. The content of deuterium in the compound according to the disclosure is much greater than the abundance in natural, and in general at least 1% of the H atoms are substituted by deuterium, preferably at least 10% of the H atoms are substituted by deuterium.

In a preferred embodiment, in the deuterated organic compound, more than 20%, preferably more than 30%, more preferably more than 40%, and most preferably more than 50% of the H atoms are substituted by deuterium.

In an embodiment of the present disclosure, HOMO, LUMO, triplet energy level (T1) and singlet energy level (S1) play a key role in the energy level structure of the organic material. The determination of these energy levels is introduced as follows.

HOMO and LUMO energy levels can be measured by photoelectric effects, such as XPS (X-ray photoelectron spectroscopy) and UPS (UV photoelectron spectroscopy), or by cyclic voltammetry (hereinafter referred to as CV). Recently, quantum chemical methods, such as density functional theory (hereinafter referred to as DFT), have also become an effective method for calculating the molecular orbital energy levels.

The triplet energy level T1 of an organic material can be measured by a low-temperature time-resolved spectroscopy or by quantum simulation calculation (for example, by Time-Dependent DFT), such as by commercial software Gaussian 03W (Gaussian Inc.) See WO2011141110 for detailed simulation methods.

The singlet energy level S1 of an organic material can be determined by the absorption spectrum or the emission spectrum, and can also be obtained by quantum simulation calculation (such as Time-dependent DFT).

It should be noted that the absolute values of HOMO, LUMO, T1 and S1 depend on the measurement method or calculation method used, even for the same method but different evaluation method. For example, different HOMO/LUMO value can be provided at the start point and peak point on a CV curve. Therefore, a reasonable and meaningful comparison should be carried out by using the same measurement method and the same evaluation method. In the description of the embodiments of the present disclosure, the values of HOMO, LUMO, T1 and S1 are based on time-dependent DFT simulation without affecting the application of other measurement or calculation methods.

In accordance with the principle of the Thermally Activated Delayed Fluorescence Materials TADF (see Adachi et al., Nature Vol 492, 234, (2012)), a triplet exciton of the organic compound can be internally reversely converted into a singlet exciton when the (S1–T1) of the organic compound is small enough, resulting in an efficient luminescence. In the present disclosure, this principle is considered as a possible mechanism.

A second feature of the present disclosure is (S1–T1) ≤0.35 eV for the organic compound.

In a preferred embodiment, according to the organic compound of the present disclosure, (S1–T1)≤0.35 eV, preferably ≤0.20 eV, more preferably ≤0.15 eV, and most preferably ≤0.10 eV.

In a preferred embodiment, in the deuterated organic compound, the electron donor group D includes any of the following groups:

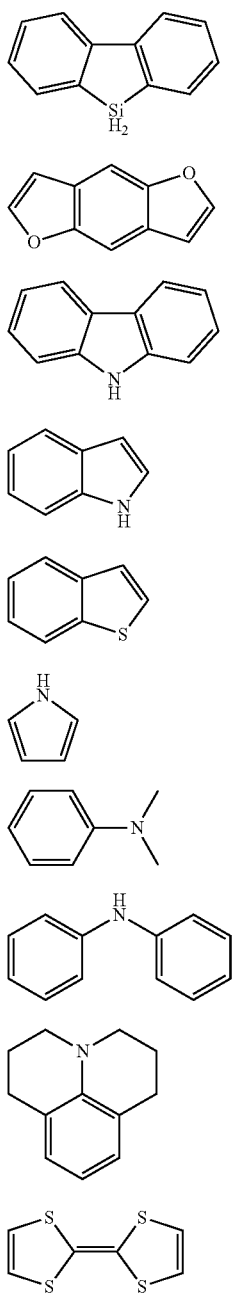

In a preferred embodiment, in the deuterated organic compound, the electron acceptor group A is selected from F, cyano and groups containing any of the following:

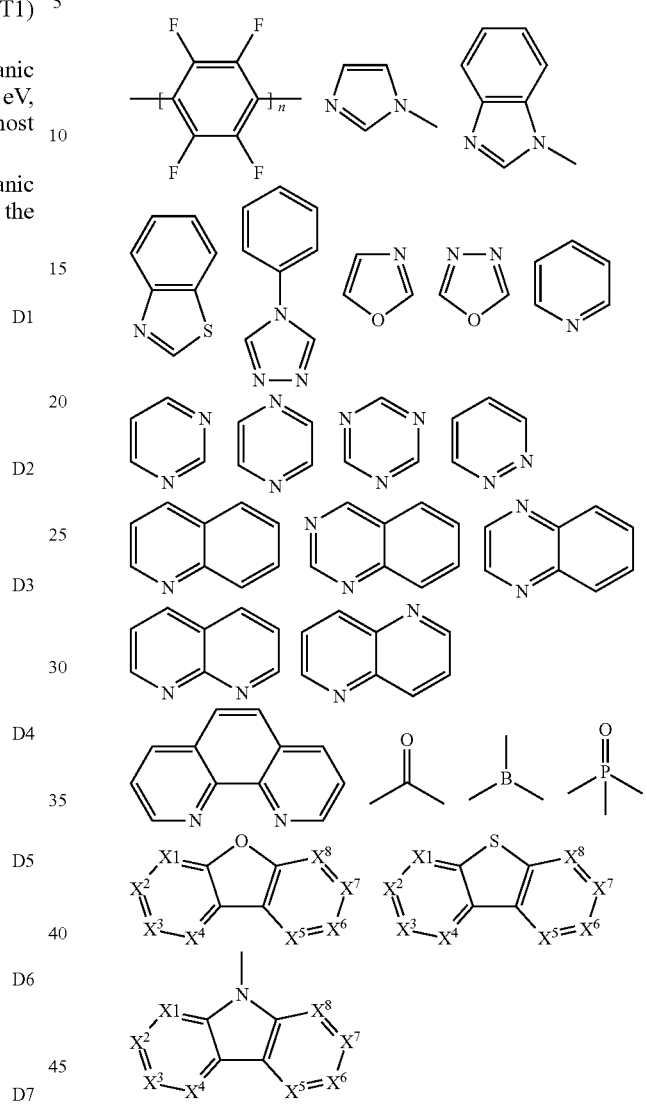

wherein n is an integer between 1 to 3, $X^1$-$X^8$ are selected from $CR^1$ or N, and at least one of $X^1$-$X^8$ is N, and wherein $R^1$ is selected from the following groups: hydrogen, alkyl, alkoxy, amino, alkenyl, alkynyl, aralkyl, heteroalkyl, aryl, and heteroaryl.

In a preferred embodiment, in the deuterated organic compound, Ar is selected from any of the following groups:

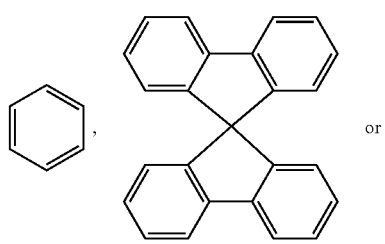

or

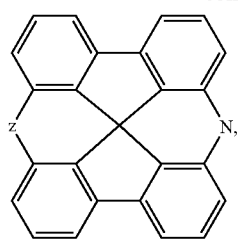
wherein z is O or S.
Some examples of materials according to the disclosure are listed below, with one or more H being substituted by deuterium:
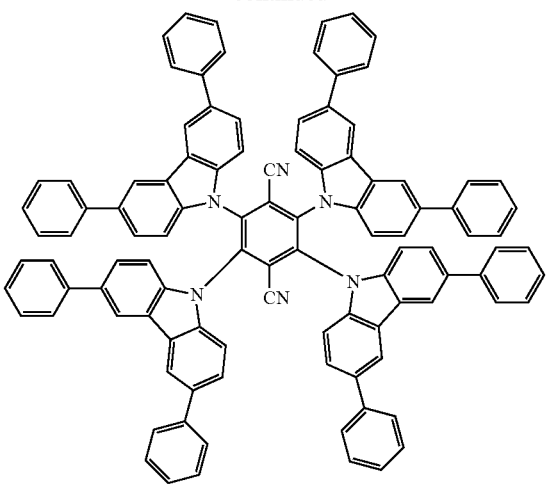
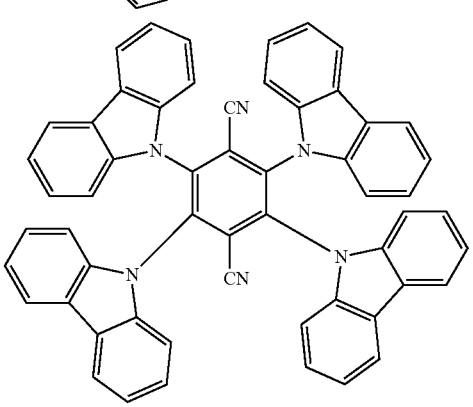
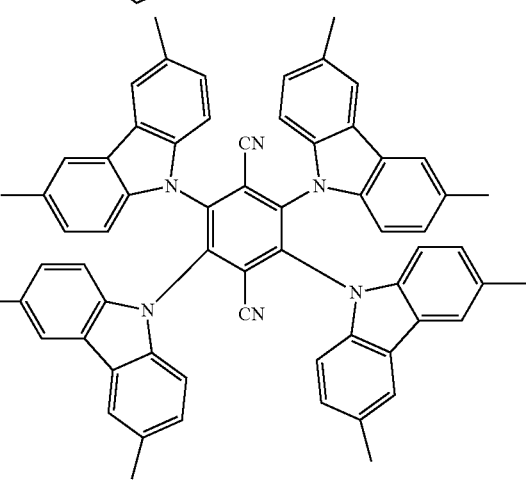
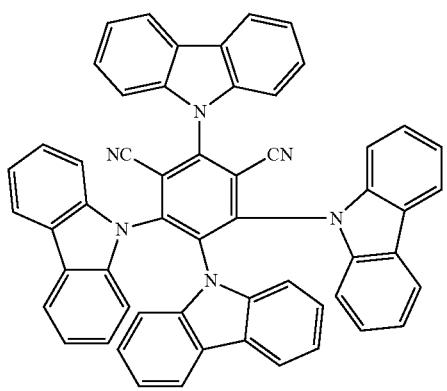
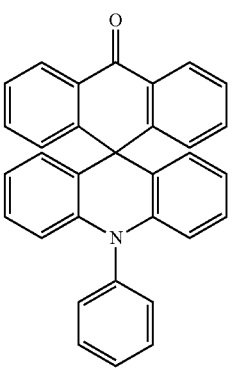

11
-continued
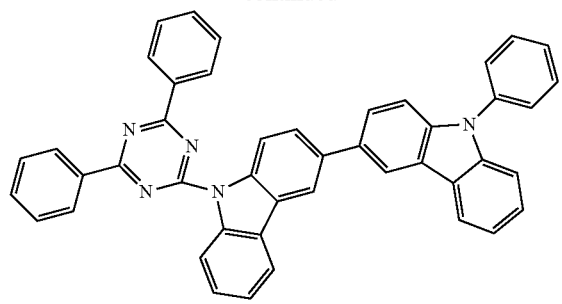
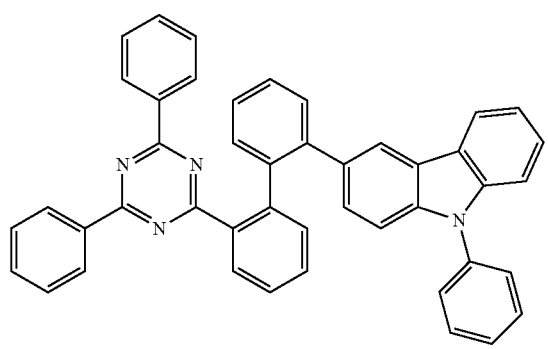
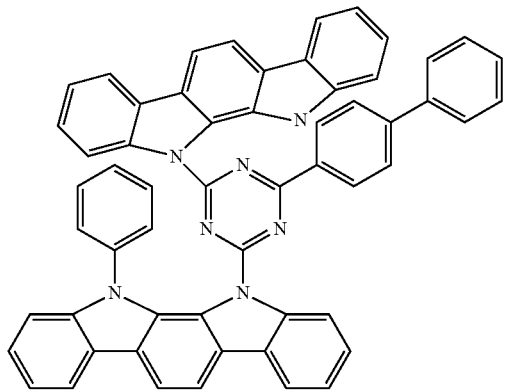
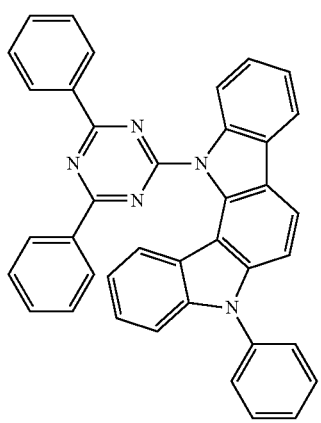
12
-continued
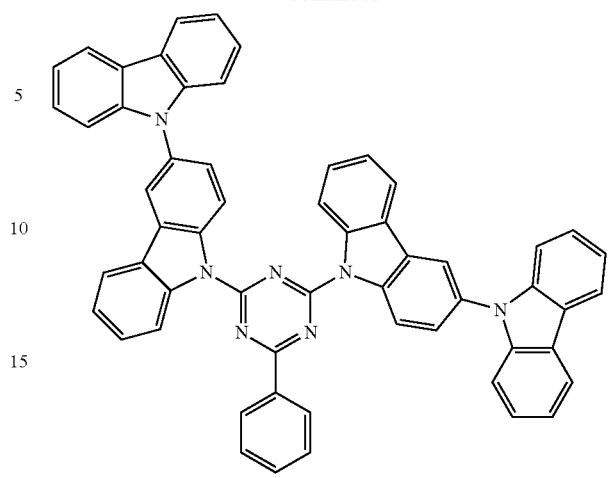
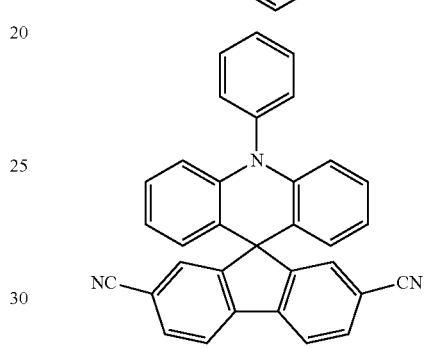
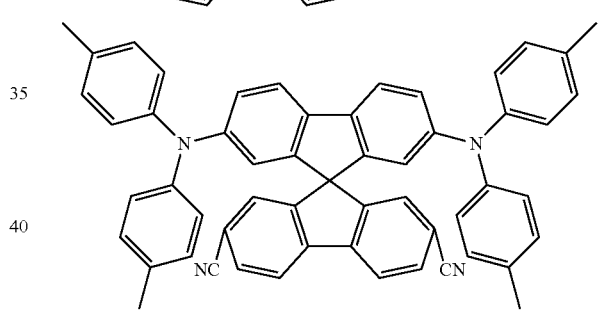
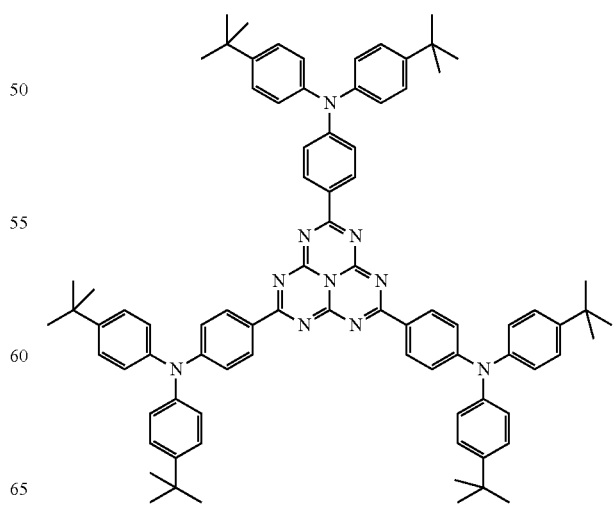

-continued

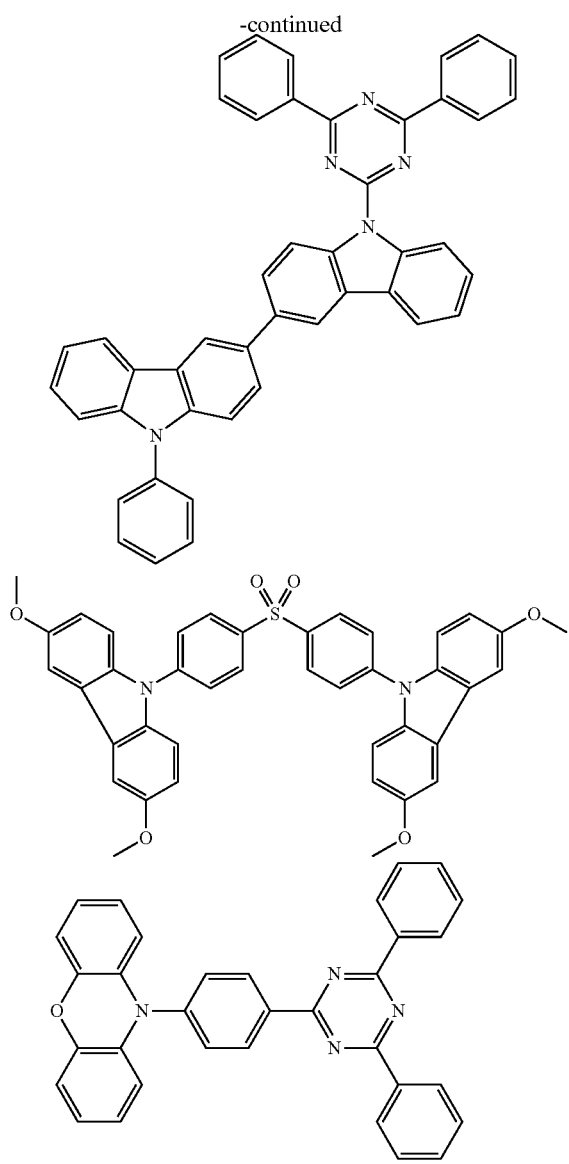

The present disclosure further provides a mixture containing at least one organic compound as described above and further containing an organic functional material selected from a hole (also called an electron hole)-injecting or hole-transport material (HIM/HTM), a hole-blocking material (HBM), an electron-injection or electron-transport material (EIM/ETM), an electron-blocking material (EBM), an organic host material (Host), a singlet emitter (fluorescent emitter), and a triplet emitter (phosphorescent emitter). These organic functional materials are described in detail, for example, in WO2010135519A1, US20090134784A1, and WO 2011110277A1. The three patent documents are specially incorporated herein by reference in their entirety.

In the embodiments of the present disclosure, the host, matrix, host material and matrix material have the same meaning and are interchangeable.

The following is a more detailed description on these organic functional materials (but not limited thereto).

1. HIM/HTM

Suitable organic HIM/HTM materials may include any one of the compounds having the following structural units:

phthalocyanines, porphyrins, amines, aryl amines, biphenyl triaryl amines, thiophenes, thiophenes such as dithiophenethiophene and thiophthene, pyrrole, aniline, carbazole, indeno-fluorene, and derivatives thereof. Other suitable HIMs also include: fluorocarbon-containing polymers; polymers comprising conductive dopants; conductive polymers such as PEDOT/PSS; self-assembled monomers such as compounds comprising phosphonic acid and silane derivatives; metal oxides, such as MoOx; metal complex, a cross-linking compound, and the like.

Examples of cyclic aromatic amine-derived compounds that may be used as HTM or HIM include, but are not limited to, the general structure as follows:

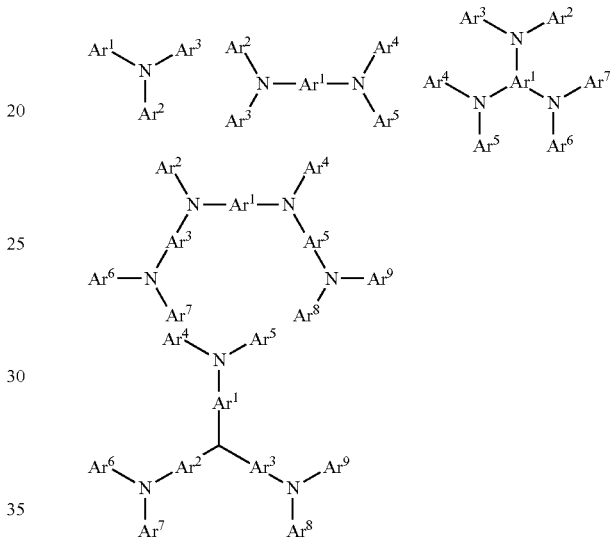

Each of $Ar^1$-$Ar^9$ is independently selected from cyclic aromatic hydrocarbon compounds, such as benzene, biphenyl, triphenyl, benzo, naphthalene, anthracene, phenalene, phenanthrene, fluorene, pyrene, chrysene, perylene, azulene; heterocyclic aryl compounds, such as triphenylamine, dibenzothiophene, dibenzofuran, furan, thiophene, benzofuran, benzothiophene, carbazole, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofuropyridine, indolocarbazole, pyridylindole, pyrrolodipyridine, furodipyridine, benzothienopyridine, thienodipyridine, benzoselenophenopyridine and selenophenodipyridine; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic rings, wherein each Ar may be further substituted and the substituents may be selected from hydrogen, alkyl, alkoxy, amino, alkene, alkyne, aralkyl, heteroalkyl, aryl and heteroaryl.

In one aspect, $Ar^1$ to $Ar^9$ may be independently selected from groups containing the following:

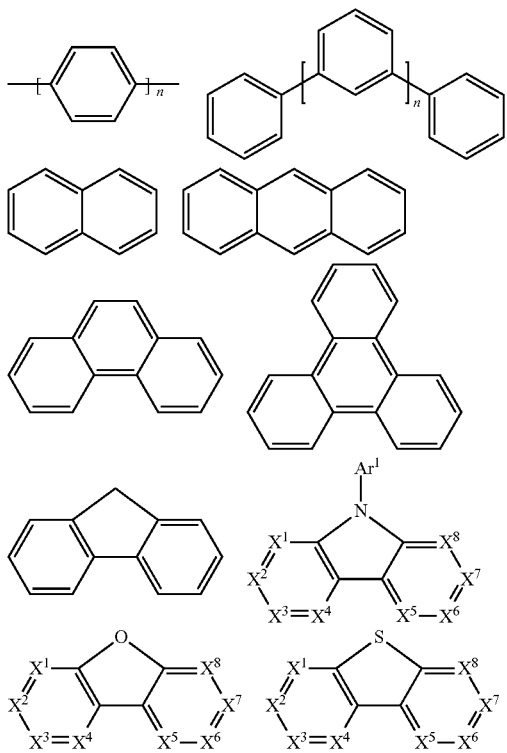

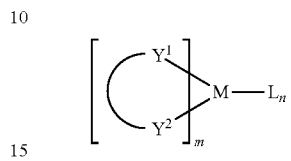

wherein n is an integer from 0 to 20; $X^1$-$X^8$ are CH or N; and $Ar^1$ have the same meaning as described above.

Additional examples of cyclic aromatic amine-derived compounds may be found in U.S. Pat. Nos. 3,567,450, 4,720,432, 5,061,569, 3,615,404, and 5,061,569.

Examples of metal complexes that may be used as HTM or HIM include, but are not limited to, the general structure as follows:

$$\left[\begin{array}{c} Y^1 \\ Y^2 \end{array}\right]_m M - L_n$$

M is a metal having an atomic weight greater than 40;
$(Y^1$-$Y^2)$ is a bidentate ligand, wherein $Y^1$ and $Y^2$ are independently selected from C, N, O, P, and S; L is an auxiliary ligand; m is an integer from 1 to the maximum coordination number of the metal; and m+n is the maximum coordination number of the metal.

In one embodiment, $(Y^1$-$Y^2)$ is a 2-phenylpyridine derivative.

In another embodiment, $(Y^1$-$Y^2)$ is a carbene ligand.

In another embodiment, M is selected from Ir, Pt, Os, and Zn.

In another aspect, the HOMO of the metal complex is greater than −5.5 eV (relative to the vacuum level).

Examples of suitable HIM/HTM compound are listed in the following table:

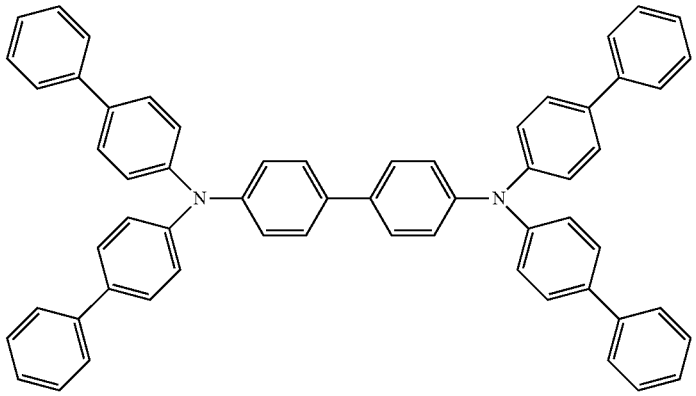

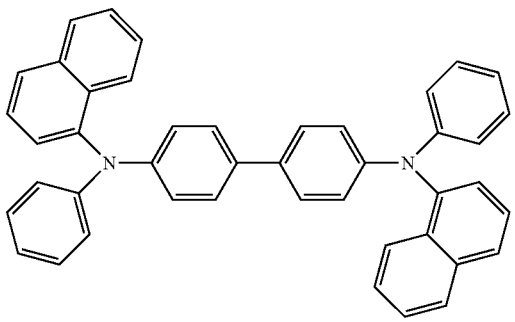

-continued

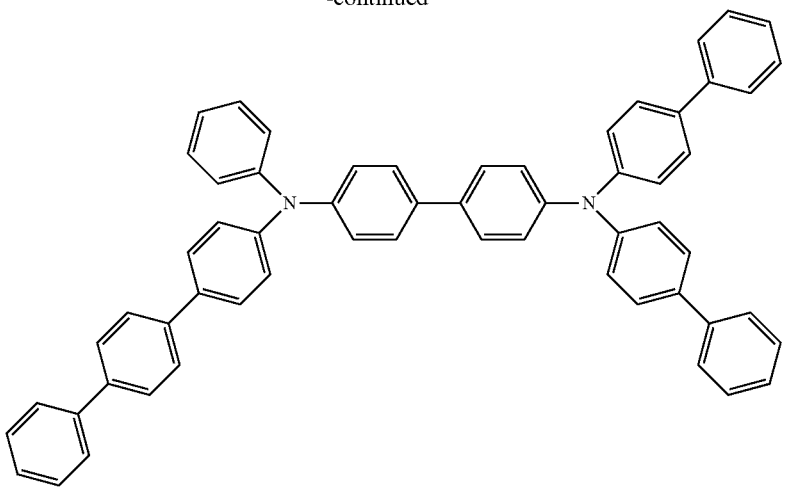

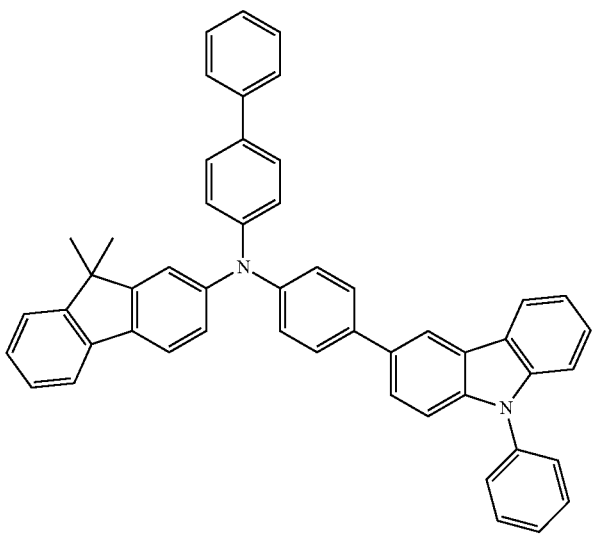

2. EIM/ETM/HBM

Examples of EIM/ETM material are not particularly limited, and any metal complex or organic compound may be used as EIM/ETM as long as they can transfer electrons. Preferred organic EIM/ETM materials may be selected from the group consisting of tris (8-quinolinolato) aluminum ($AlQ_3$), phenazine, phenanthroline, anthracene, phenanthrene, fluorene, bifluorene, spiro-bifluorene, phenylene-vinylene, triazine, triazole, imidazole, pyrene, perylene, trans-indenofluorene, cis-indenonfluorene, dibenzol-indeno-fluorene, indenonaphthalene, benzanthracene and their derivatives.

The hole-blocking layer (HBL) is typically used to block holes from adjacent functional layers, particularly light-emitting layers. In contrast to a light-emitting device without a barrier layer, the presence of HBL usually leads to an increase in luminous efficiency. The hole-blocking material (HBM) of the hole-blocking layer (HBL) requires a lower HOMO than the adjacent functional layer, such as the light-emitting layer. In a preferred embodiment, the HBM has a greater energy level of excited state than the adjacent light-emitting layer, such as a singlet or triplet, depending on the emitter. In another preferred embodiment, the HBM has an electron-transport function. Typically, EIM/ETM materials with deep HOMO levels may be used as HBM.

In another aspect, compounds that may be used as EIM/ETM/HBM compounds may be molecules comprising at least one of the following groups:

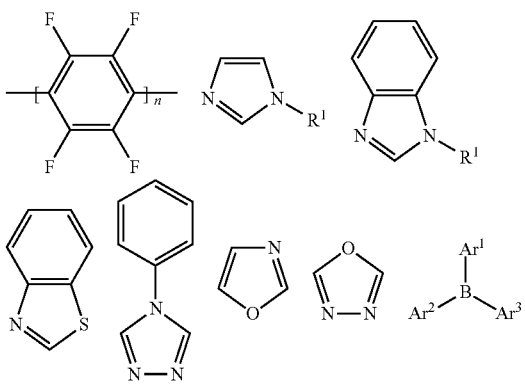

-continued

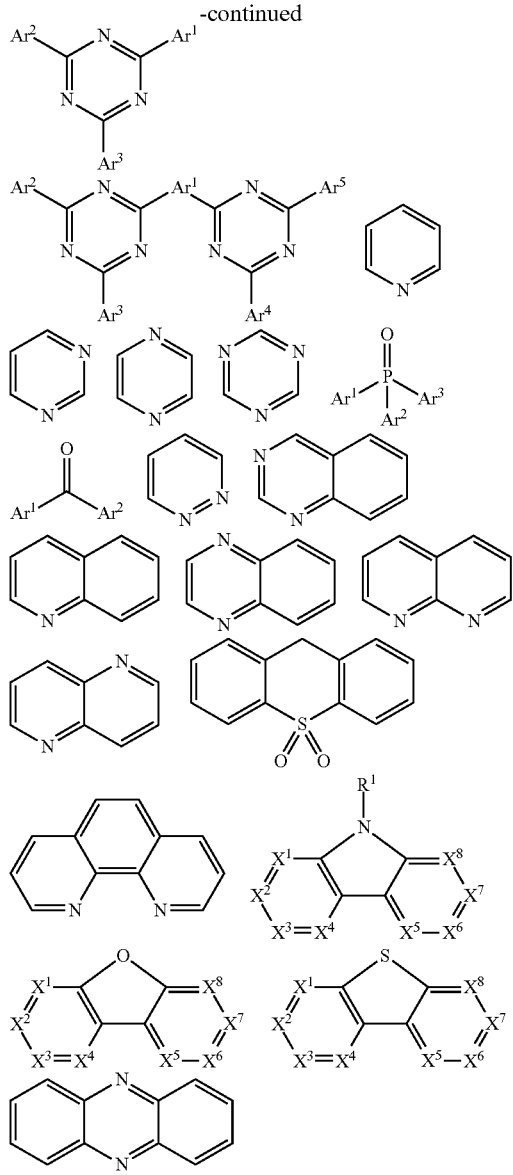

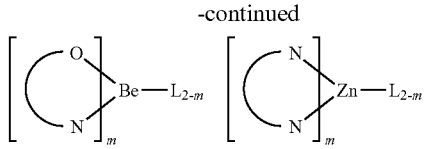

-continued (O—N) or (N—N) is a bidentate ligand, wherein the metal coordinates with O, N, or N, N; L is an auxiliary ligand; and m is an integer whose value is from 1 to the maximum coordination number of the metal.

Examples that can be used as suitable ETM compounds are listed in the table below:

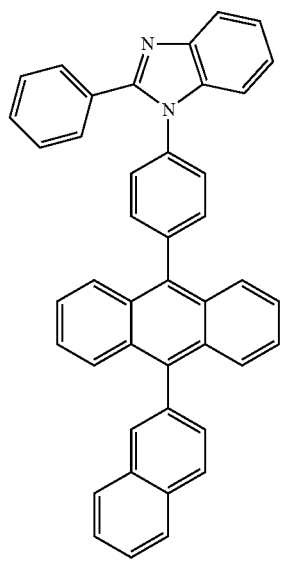

$R^1$ is selected from the group consisting of hydrogen, alkyl, alkoxy, amino, alkene, alkyne, aralkyl, heteroalkyl, aryl and heteroaryl, which have the same meaning as $Ar^1$ and $Ar^2$ in HTM as described above when they are aryl or heteroaryl;

$Ar^1$-$Ar^5$ has the same meaning as $Ar^1$ in HTM as described above;

n is an integer from 0 to 20; and $X^1$-$X^8$ are selected from $CR^1$ or N.

In yet another aspect, examples of metal complexes that may be used as EIM/ETM include, but are not limited to, the following general structure:

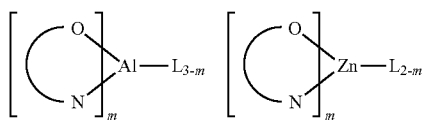

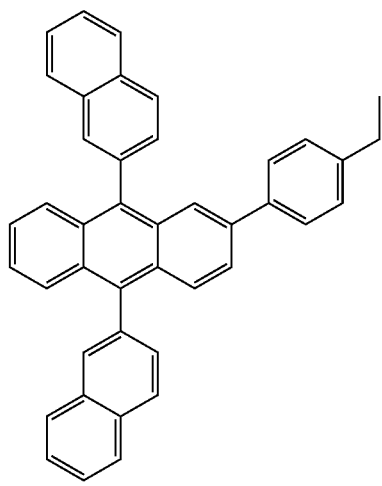

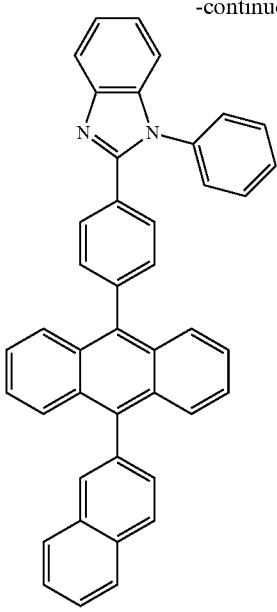

In another preferred embodiment, the organic alkali metal compound may be used as the EIM. In the present disclosure, the organic alkali metal compound may be understood as a compound having at least one alkali metal, i.e., lithium, sodium, potassium, rubidium, and cesium, and further comprising at least one organic ligand.

Suitable organic alkali metal compounds include the compounds described in U.S. Pat. No. 7,767,317 B2, EP 1941562B1 and EP 1144543B1.

The organic alkali metal compound preferably selected are a compound of the following formula:

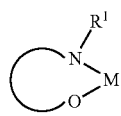

wherein R¹ has the same meaning as described above, and the arc represents two or three atoms and the bond to form a 5- or 6-membered ring with metal M when necessary, while the atoms may be substituted with one or more R¹; and wherein M is an alkali metal selected from lithium, sodium, potassium, rubidium, and cesium.

The organic alkali metal compound may be in the form of a monomer, as described above, or in the form of an aggregate, for example, two alkali metal ions with two ligands, 4 alkali metal ions and 4 ligands, 6 alkali metal ions and 6 ligand, or in other forms.

The preferred organic alkali metal compound preferably selected is a compound of the following formula:

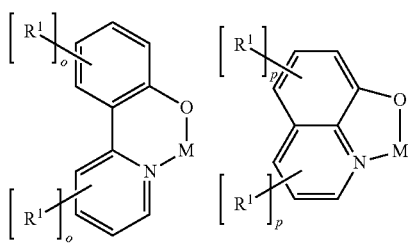

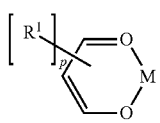

wherein the symbols used are as defined above, and in addition:

o, each time it may be the same or different, selected from 0, 1, 2, 3 or 4; and p, each time it may be the same or different, selected from 0, 1, 2 or 3.

In a preferred embodiment, the alkali metal M is selected from the group consisting of lithium, sodium, potassium, more preferably lithium or sodium, and most preferably lithium.

In a preferred embodiment, the organic alkali metal compound is used in the electron-injection layer; and more preferably, the electron-injection layer consists of the organic alkali metal compound.

In another preferred embodiment, the organic alkali metal compound is doped into other ETMs to form an electron-transport layer or an electron-injection layer, more preferably an electron-transport layer.

Examples of suitable organic alkali metal compounds are listed in the following table:

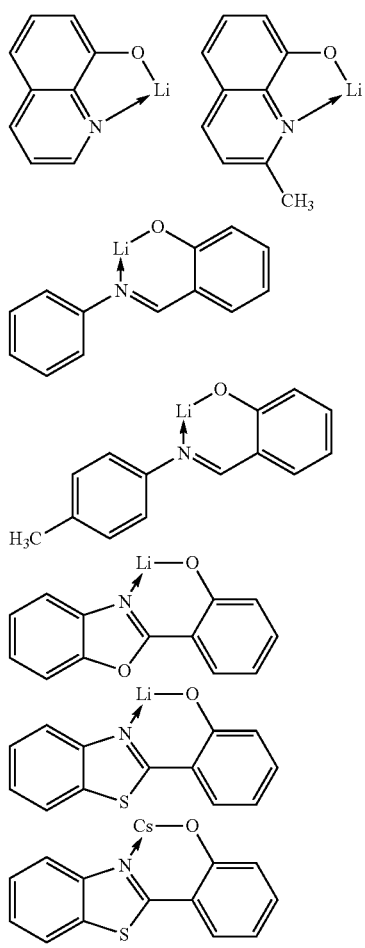

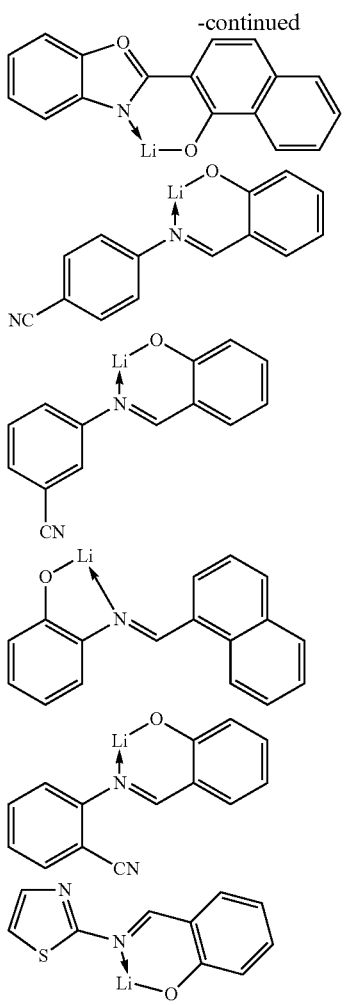

3. Triplet Host Materials

Examples of a triplet host material are not particularly limited and any metal complex or organic compound may be used as the host material as long as its triplet energy is greater than that of the light emitter, especially a triplet emitter or phosphorescent emitter.

Examples of metal complexes that may be used as triplet hosts may include, but are not limited to, the general structure as follows:

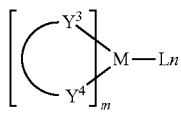

wherein M is a metal; ($Y^3$-$Y^4$) is a bidentate ligand, $Y^3$ and $Y^4$ are independently selected from C, N, O, P, and S; L is an auxiliary ligand; m is an integer with the value from 1 to the maximum coordination number of the metal; and, m+n is the maximum number of coordination of the metal.

In a preferred embodiment, the metal complex which may be used as the triplet host has the following form:

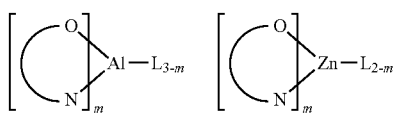

(O—N) is a bidentate ligand in which the metal is coordinated to O and N atoms.

In one embodiment, M may be selected from Ir and Pt.

Examples of organic compounds that may be used as triplet host are selected from: compounds containing cyclic aryl groups, such as benzene, biphenyl, triphenyl, benzo, and fluorene; compounds containing heterocyclic aryl groups, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, or a combination thereof; and groups containing 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic ring, wherein each Ar may be further substituted and the substituents may be selected from hydrogen, alkyl, alkoxy, amino, alkene, alkyne, aralkyl, heteroalkyl, aryl and heteroaryl.

In a preferred embodiment, the triplet host material is selected from compounds comprising at least one of the following groups:

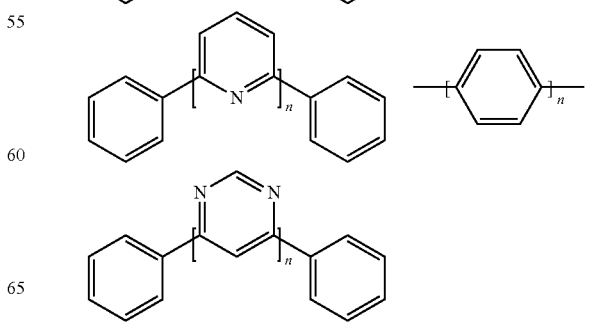

-continued

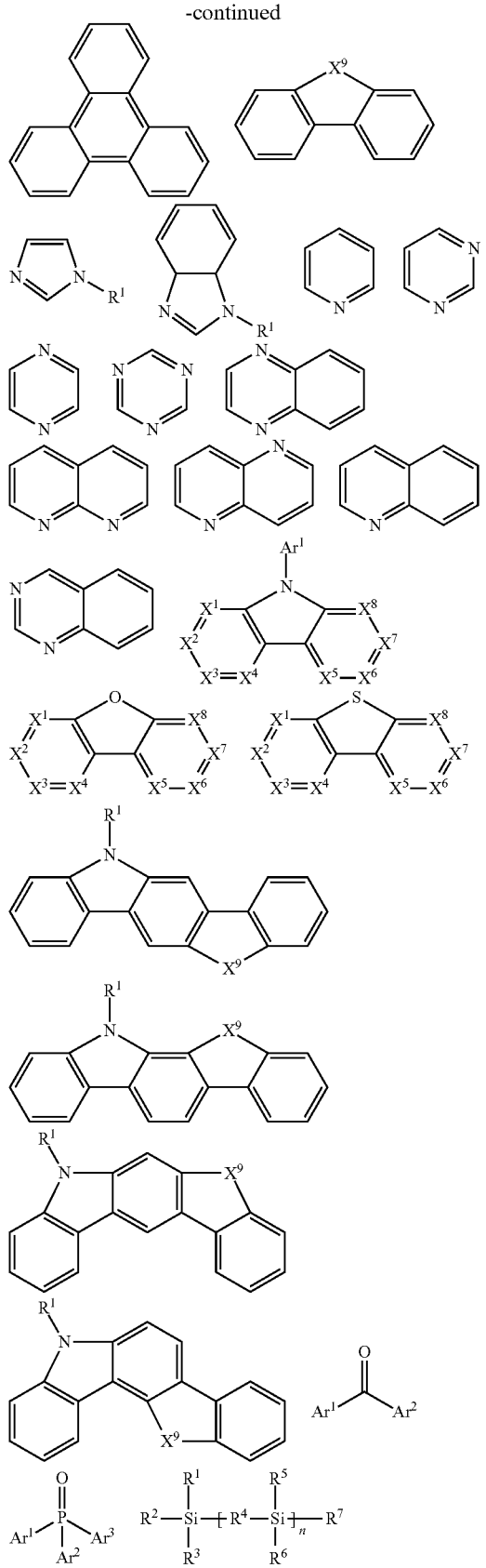

R$^1$-R$^7$ may be independently selected from the group consisting of hydrogen, alkyl, alkoxy, amino, alkene, alkyne, aralkyl, heteroalkyl, aryl and heteroaryl, which have the same meaning as Ar$^1$ and Ar$^2$ described above when they are aryl or heteroaryl; and n is an integer from 0 to 20; X$^1$-X$^8$ are selected from CH or N; and X$^9$ is selected from CR$^1$R$^2$ or NR$^1$.

Examples of suitable triplet host materials are listed in the following table:

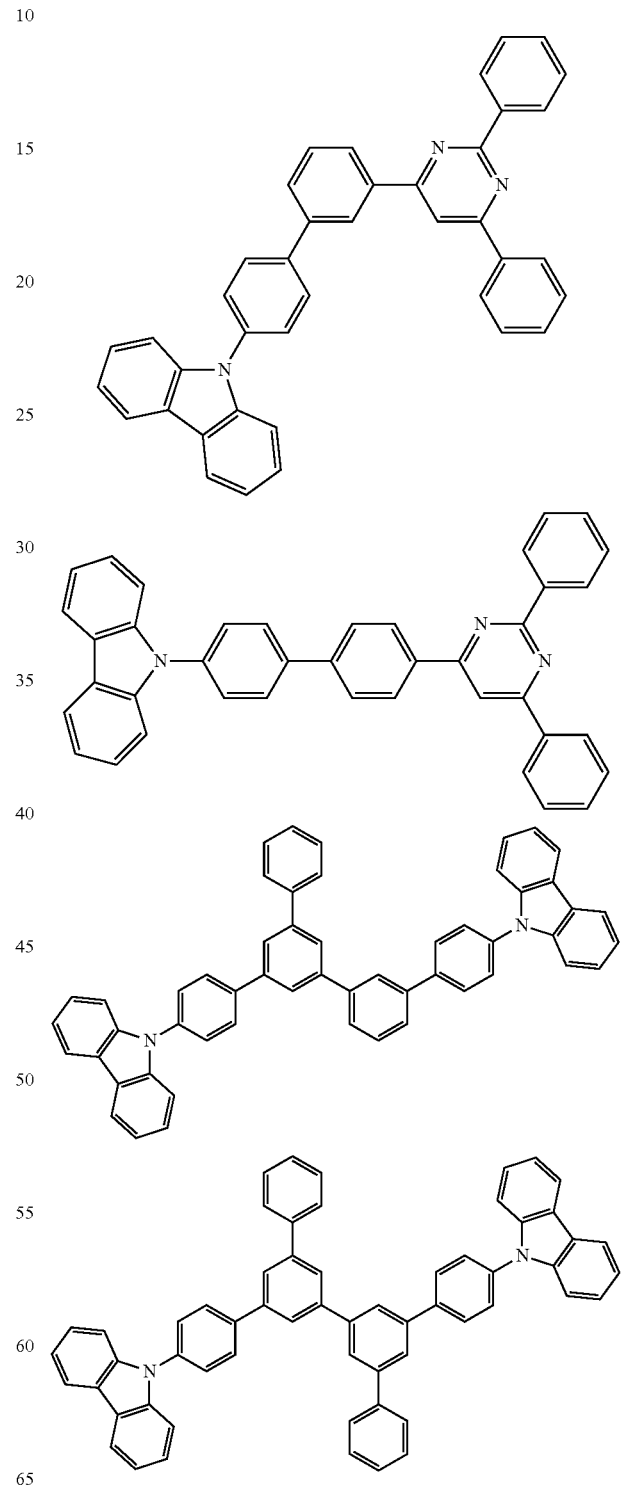

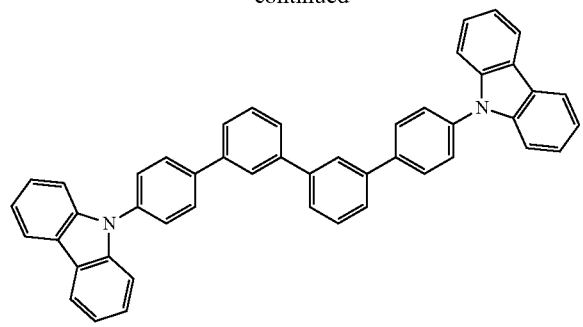

4. Singlet Host Material

Examples of singlet host material are not particularly limited and any organic compound may be used as the host as long as its singlet state energy is greater than that of the light emitter, especially the singlet emitter or fluorescent light emitter.

Examples of organic compounds used as singlet host materials may be selected from: cyclic aryl compounds, such as benzene, biphenyl, triphenyl, benzo, naphthalene, anthracene, phenalene, phenanthrene, fluorene, pyrene, chrysene, perylene, azulene; heterocyclic aryl compounds, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic rings.

In a preferred embodiment, the monomorphic host material is selected from compounds comprising at least one of the following groups:

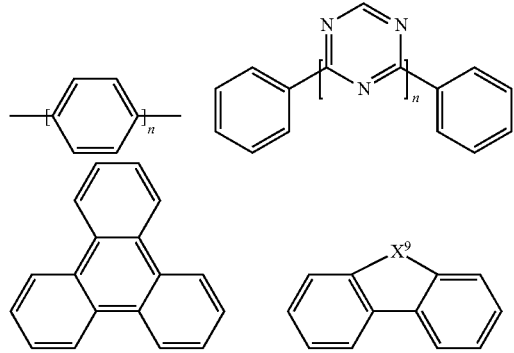

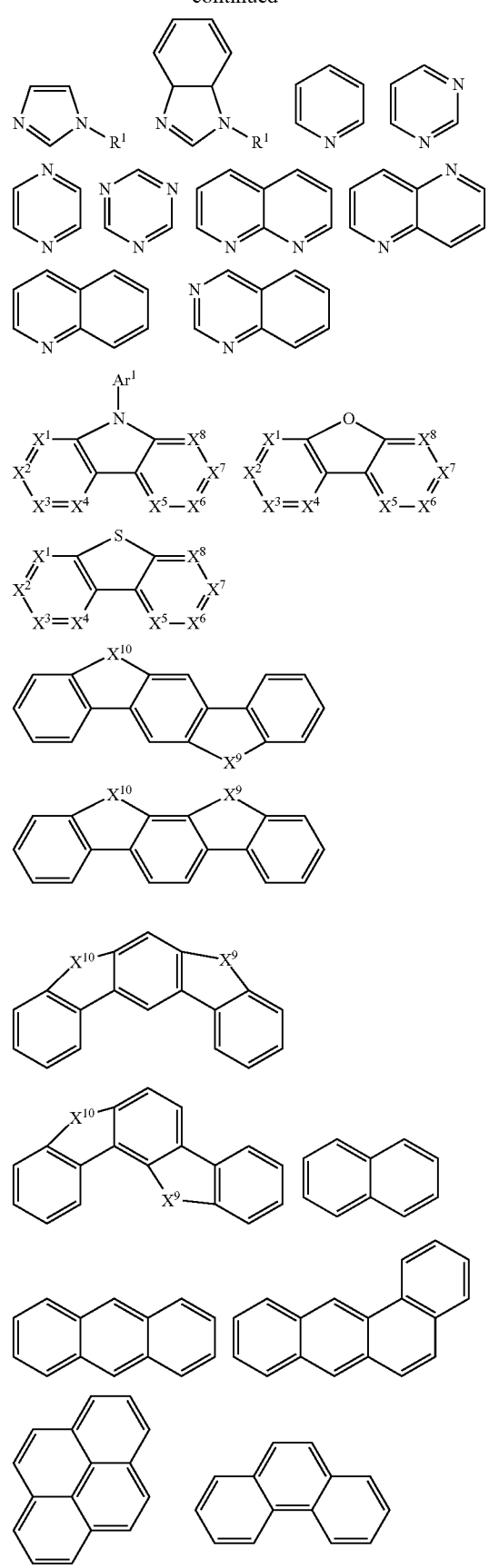

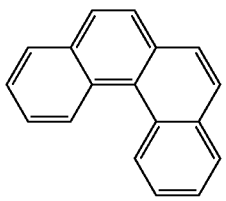

R¹ may be independently selected from the group consisting of hydrogen, alkyl, alkoxy, amino, alkene, alkyne, aralkyl, heteroalkyl, aryl and heteroaryl; Ar¹ is aryl or heteroaryl and has the same meaning as Ar¹ defined in the HTM above; and n is an integer from 0 to 20; $X^1$-$X^8$ are selected from CH or N; $X^9$ and $X^{10}$ are selected from $CR^1R^2$ or $NR^1$.

Examples of a suitable singlet host material are listed in the following table:

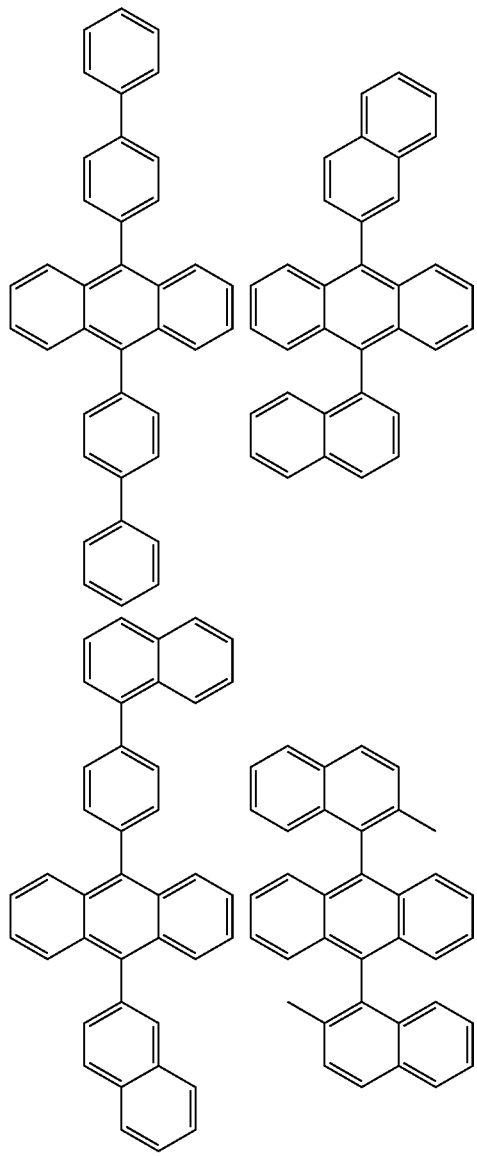

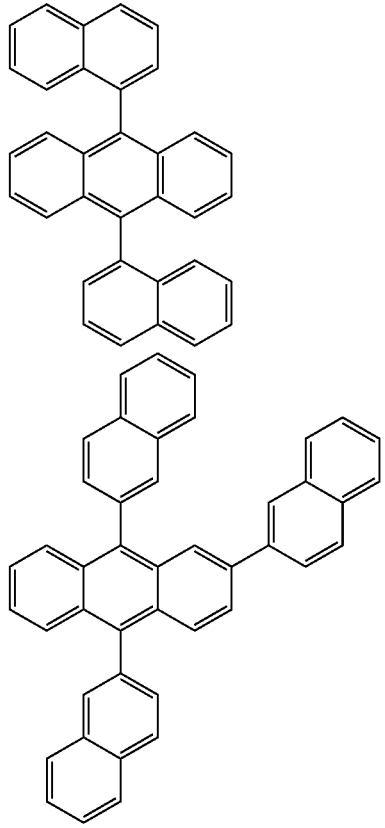

4. Singlet Emitter

The singlet emitter tends to have a longer conjugate π-electron system. To date, there have been many examples, such as, but not limited to, styrylamine and its derivatives, and indenofluorene and its derivatives disclosed in WO2008/006449 and WO2007/140847.

In a preferred embodiment, the singlet emitter may be selected from the group consisting of monostyrylamines, distyrylamines, tristyrylamines, tetrastyrylamines, styrylphosphines, styryl ethers, and arylamines.

Mono styrylamine refers to a compound which comprises one unsubstituted or substituted styryl group and at least one amine, most preferably an aryl amine. Distyrylamine refers to a compound comprising two unsubstituted or substituted styryl groups and at least one amine, most preferably an aryl amine. Ternarystyrylamine refers to a compound which comprises three unsubstituted or substituted styryl groups and at least one amine, most preferably an aryl amine. Quaternarystyrylamine refers to a compound comprising four unsubstituted or substituted styryl groups and at least one amine, most preferably an aryl amine. Preferred styrene is stilbene, which may be further substituted. The corresponding phosphines and ethers are defined similarly to amines. Aryl amine or aromatic amine refers to a compound comprising three unsubstituted or substituted cyclic or heterocyclic aryl systems directly attached to nitrogen. At least one of these cyclic or heterocyclic aryl systems is preferably selected from fused ring systems and most preferably has at least 14 aryl ring atoms. Among the preferred examples are aryl anthramine, aryl anthradiamine, aryl pyrene amines, aryl pyrene diamines, aryl chrysene amines and aryl chrysene diamine. Aryl anthramine refers to a compound in which one diarylamino group is directly attached to anthracene, most preferably at position 9. Aryl anthradiamine refers to a compound in which two diarylamino groups are directly attached to anthracene, most preferably at positions 9, 10. Aryl pyrene amines, aryl pyrene diamines, aryl chrysene amines and aryl chrysene diamine are similarly defined, wherein the diarylarylamino group is most preferably attached to position 1 or 1 and 6 of pyrene.

Examples of singlet emitter based on vinylamine and arylamine are also preferred examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1957606 A1, and US 2008/0113101 A1. The patent documents listed above are specially incorporated herein by reference in their entirety.

Examples of singlet light emitters based on distyrylbenzene and its derivatives may be found in, for example, U.S. Pat. No. 5,121,029.

More preferred singlet emitter is selected from indenofluorene-amine and indenofluorene-diamine, such as those disclosed in WO 2006/122630; benzoindenofluorene-amine and benzoindenofluorene-diamine, such as those disclosed in WO 2008/006449, and dibenzoindenofluorene-amine and dibenzoindenofluorene-diamine, such as those disclosed in WO2007/140847.

Other materials useful as singlet emitters include polycyclic aryl compounds, especially one selected from the derivatives of the following compounds: anthracenes such as 9,10-di-naphthylanthracene, naphthalene, tetraphenyl, phenanthrene, perylene such as 2,5,8,11-tetra-t-butylatedylene, indenoperylene, phenylenes such as 4,4'-(bis (9-ethyl-3-carbazovinylene)-1,1'-biphenyl, periflanthene, decacyclene, coronene, fluorene, spirobifluorene, arylpyren (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanoethylene)-6-(4-dimethylaminostyryl-2-methyl)-4H-pyrane (DCM), thiapyran, bis (azinyl) imine-boron compounds (US 2007/0092753 A1), bis (azinyl) methene compounds, carbostyryl compounds, oxazone, benzoxazole, benzothiazole, benzimidazole, and diketopyrrolopyrrole. Some singlet emitter materials may be found in the following patent documents: US 20070252517 A1, U.S. Pat. Nos. 4,769,292, 6,020,078, US 2007/0252517 A1, and US 2007/0252517 A1. The patent documents listed above are specially incorporated herein by reference in their entirety.

Examples of suitable singlet emitters are listed in the following table:

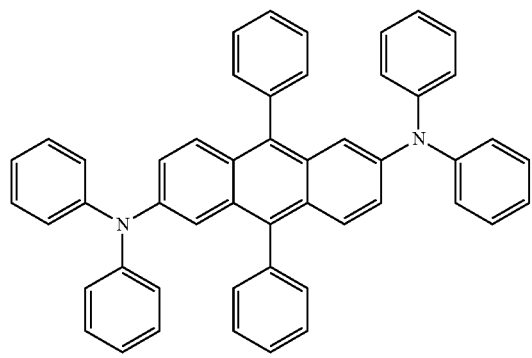

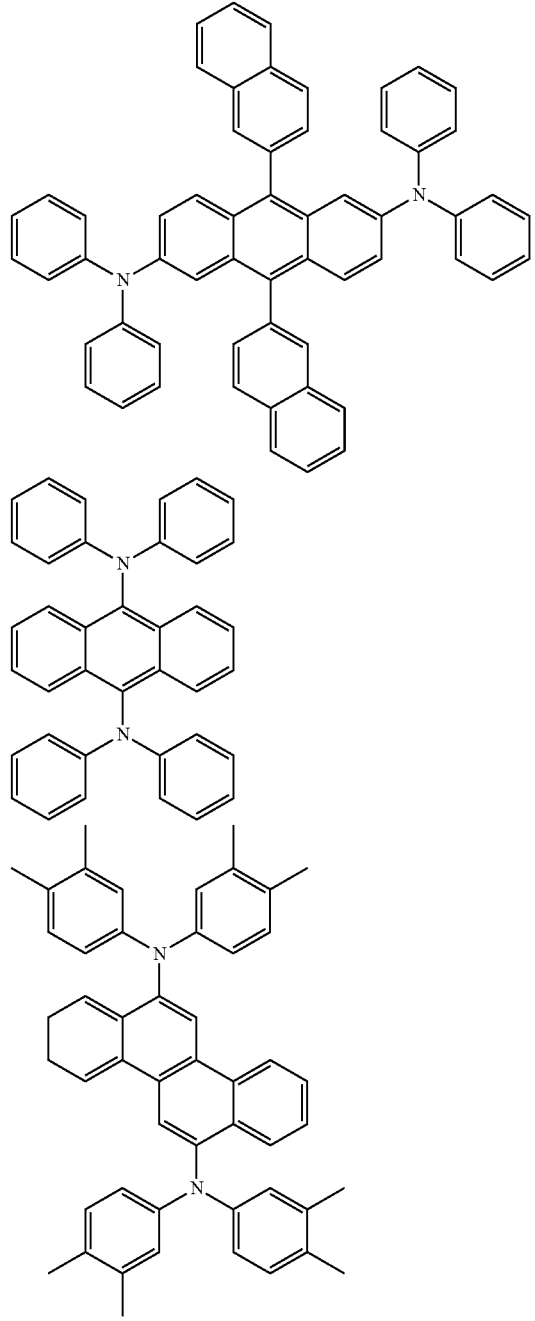

5. Triplet Emitter

The triplet emitter is also called a phosphorescent emitter. In a preferred embodiment, the triplet emitter is a metal complex of the general formula M (L) n, wherein M may be a metal atom; L may be a same or different ligand each time it is present, and may be bonded or coordinated to the metal atom M at one or more positions; n may be an integer greater than 1, preferably 1, 2, 3, 4, 5 or 6. Alternatively, these metal complexes may be attached to a polymer by one or more positions, most preferably through an organic ligand.

In a preferred embodiment, the metal atom M may be selected from the group consisting of transition metal elements or lanthanides or actinides, preferably Ir, Pt, Pd, Au, Rh, Ru, Os, Sm, Eu, Gd, Tb, Dy, Re, Cu or Ag, and particularly preferably Os, Ir, Ru, Rh, Re, Pd, or Pt.

Preferably, the triplet emitter comprises a chelating ligand, i.e., a ligand, coordinated to the metal by at least two bonding sites, and it is particularly preferred that the triplet emitter comprises two or three identical or different bidentate or multidentate ligand. Chelating ligands help to improve stability of metal complexes.

Examples of organic ligands may be selected from the group consisting of phenylpyridine derivatives, 7,8-benzoquinoline derivatives, 2 (2-thienyl) pyridine derivatives, 2 (1-naphthyl) pyridine derivatives, or 2 phenylquinoline derivatives. All of these organic ligands may be substituted, for example, with fluoromethyl or trifluoromethyl. The auxiliary ligand may be preferably selected from acetylacetonate or picric acid.

In a preferred embodiment, the metal complex which may be used as the triplet emitter has the following form:

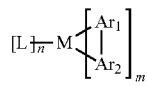

wherein M is a metal selected from the group consisting of transition metal elements or lanthanides or actinides; $Ar^1$ may be the same or different cyclic group each time it is present, which comprises at least one donor atom, that is, an atom with a lone pair of electrons, such as nitrogen atom or phosphorus atom, which is coordinated to the metal through its ring group; $Ar^2$ may be the same or different cyclic group comprising at least one C atom and is coordinated to the metal through its ring group; $Ar^1$ and $Ar^2$ are covalently bonded together, wherein each of them may carry one or more substituents which may also be joined together by substituents; L may be the same or different at each occurrence and is an auxiliary ligand, preferably a bidentate chelating ligand, and most preferably a monoanionic bidentate chelating ligand; m is 1, 2 or 3, preferably 2 or 3, and particularly preferably 3; and, N is 0, 1, or 2, preferably 0 or 1, particularly preferably 0.

Examples of triplet emitter materials and their application may be found in the following patent documents and references: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1. The patent documents and references listed above are specially incorporated herein by reference in their entirety.

6. Polymers

In some embodiments, the organic functional materials described above, including HIM, HTM, ETM, EIM, Host, fluorescent emitter, and phosphorescent emitters, may be in the form of polymers.

In a preferred embodiment, the polymer suitable for the present disclosure is a conjugated polymer. In general, the conjugated polymer has the general formula:

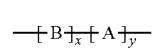

Chemical Formula 1 wherein B, A may be independently selected as the same or different structural elements in multiple occurrences B: a π-conjugated structural unit with relatively large energy gap, also referred to as backbone unit, which may be selected from monocyclic or polycyclic aryl or heteroaryl, preferably in the form of benzene, biphenylene, naphthalene, anthracene, phenanthrene, dihydrophenanthrene, 9,10-dihydrophenanthroline, fluorene, difluorene, spirobifluorene, p-phenylenevinylene, trans-indenofluorene, cis-indenofluorene, dibenzol-indenofluorene, indenonaphthalene and derivatives thereof;

A: a π-conjugated structural unit with relatively small energy gap, also referred to as a functional unit, which, according to different functional requirements, may be selected from the structural units of the above-mentioned hole-injection or hole-transport material (HIM/HTM), hole-blocking material (HBM), electron-injection or electron-transport material (EIM/ETM), electron-blocking material (EBM), organic host material (Host), singlet emitter (fluorescent emitter), multiplet emitter (phosphorescent emitter); and x, y:>0, and x+y=1.

In a preferred embodiment, the polymer HTM material is a homopolymer, and the preferred homopolymer is selected from polythiophene, polypyrrole, polyaniline, polybenzene triarylamine, polyvinylcarbazole and their derivatives.

In another preferred embodiment, the polymer HTM material is a conjugated copolymer represented by Chemical Formula 1, wherein A: a functional group having a hole-transport capacity, which may be selected from structural units comprising the above-mentioned hole-injection or hole-transport material (HIM/HTM); in a preferred embodiment, A is selected from the group consisting of amine, benzenesulfonates, thiophenes and thiophenes such as dithienothiophene and thiophene, pyrrole, aniline, carbazole, indolecarbazole, indenobenzofluorene, pentacene, phthalocyanine, porphyrins and their derivatives; and x,y:>0, and x+y=1; usually y≥0.10, preferably ≥0.15, more preferably ≥0.20, preferably x=y=0.5.

Examples of suitable conjugated polymers that can be used as HTM are listed below:

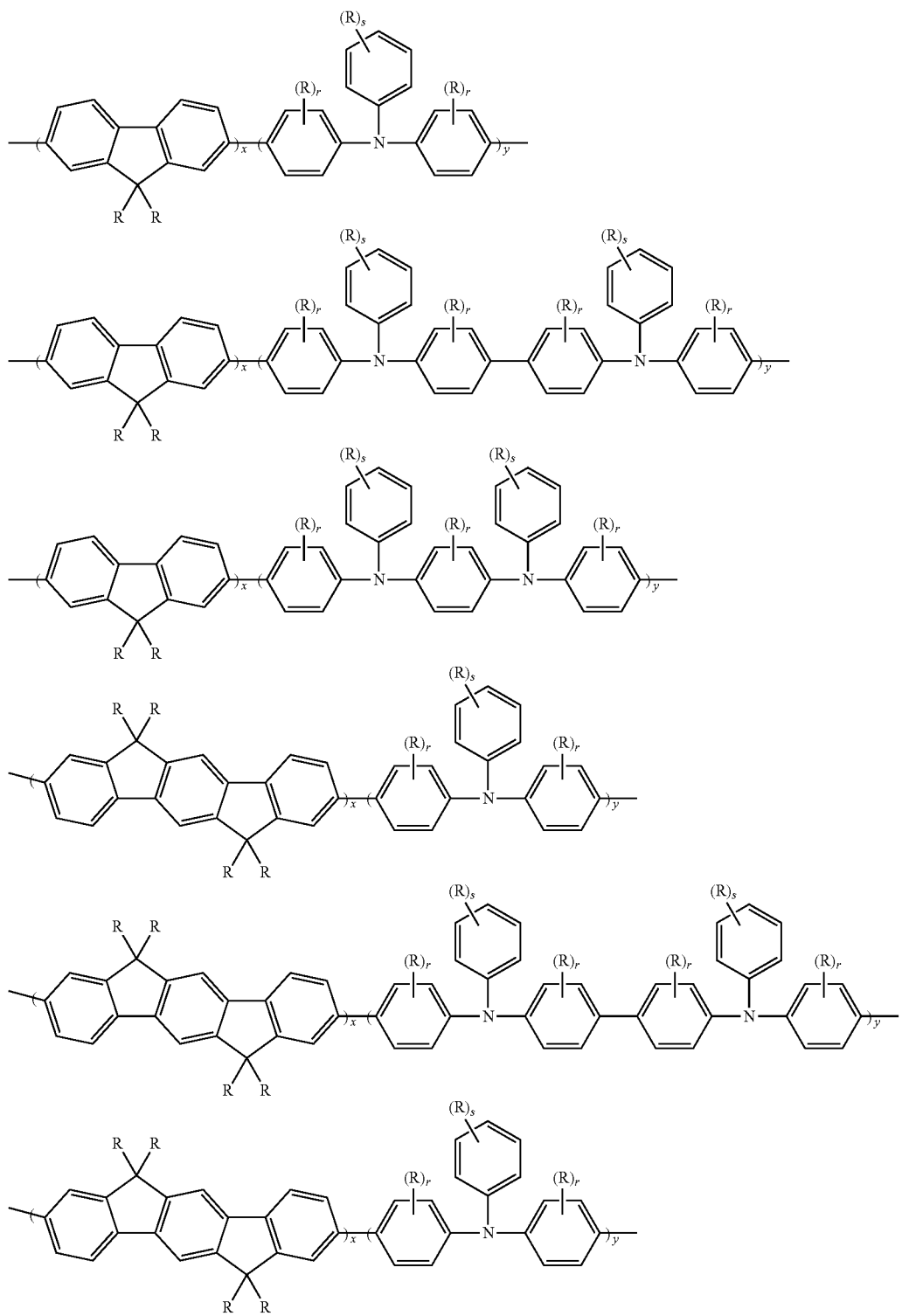

wherein R are each independently hydrogen; a straight chain alkyl group, an alkoxy group or a thioalkoxy group having 1 to 20 C atoms; a branched or cyclic alkyl group, an alkoxy group or a thioalkoxy group or a silyl group having 3 to 20 C atoms; or a substituted keto group having 1 to 20 C atoms; an alkoxycarbonyl group having 2 to 20 C atoms; aryloxycarbonyl group having 7 to 20 C atoms; a cyano group (—CN); a carbamoyl group (—C(=O)NH$_2$); a haloyl group (—C(=O)—X wherein X represents a halogen atom); a formyl group (—C(=O)—H); an isocyanato group; an isocyanate group; a thiocyanate group; an isothiocyanate group; a hydroxyl group; a nitro group; a CF$_3$ group; Cl; Br; F; a crosslinkable group; a substituted or unsubstituted aromatic or heteroaromatic ring system having 5 to 40 ring atoms; or an aryloxy or heteroaryloxy group having 5 to 40 ring atoms, or a combination of these systems in which one or more groups R may form a single ring or polycyclic aliphatic or aromatic ring system between one another and/or with a ring bonded to the group R;

r is 0, 1, 2, 3 or 4;
s is 0, 1, 2, 3, 4 or 5; and
x,y:>0, and x+y=1; usually y=y≥0.10, preferably ≥0.15, more preferably ≥0.20, preferably x=y=0.5.

Another preferred type of organic ETM material is a polymer having an electron transporting capacity comprising a conjugated polymer and a nonconjugated polymer.

The preferred polymer ETM material is a homopolymer, which is selected from the group consisting of polyphenanthrene, polyphenanthroline, polyindenyl fluorene, poly spiethylene fluorene, polyfluorene and their derivatives.

The preferred polymer ETM material is a conjugated copolymer represented by Chemical Formula 1, wherein A can be independently selected in the same or different forms in multiple occurrences:

A: a functional group having a electron transporting capacity, preferably selected from the group consisting of tris (8-quinolinolato) aluminum, benzene, biphenylene, naphthalene, anthracene, phenanthrene, dihydrophenanthrene, fluorene, difluorene, spirobifluorene, p-phenylenevinylene, pyrene, perylene, 9,10-dihydrophenanthroline, phenoxazine, phenanthroline, trans-indenofluorene, cis-indenonfluorene, dibenzol-indenofluorene, indenonaphthalene, benzanthracene and their derivatives; and x,y:>0, and x+y=1; usually y≥0.10, preferably ≥0.15, more preferably ≥0.20, preferably x=y=0.5.

In a preferred embodiment, light-emitting polymers are conjugated polymers having the following formula:

Chemical formula 2

B: as defined in chemical formula 1;
A1: a functional group having a hole or electron transporting capacity, which may be selected from structural units of the above-mentioned hole-injection or hole-transport material (HIM/HTM), or electron injection or transport material;
A2: a group having light emitting function, which may be selected from structural units of singlet emitter (fluorescent emitter) or multiplet emitter (phosphorescent emitter); and
x,y,z:>0, and x+y+z=1;

Examples of light-emitting polymers are disclosed in WO2007043495, WO2006118345, WO2006114364, WO2006062226, WO2006052457, WO2005104264, WO2005056633, WO2005033174, WO2004113412, WO2004041901, WO2003099901, WO2003051092, WO2003020790, WO2003020790, US2020040076853, US2020040002576, US2007208567, US2005962631, EP201345477, EP2001344788, and DE102004020298. The above patent documents are specially incorporated herein by reference in their entirety.

In another embodiment, the polymers suitable for the present disclosure are non-conjugated polymers. The non-conjugated polymer may be the backbone with all functional groups on the side chain. Such non-conjugated polymers for use as phosphorescent host or phosphorescent emitter materials are disclosed in patent applications such as U.S. Pat. No. 7,250,226 B2, JP2007059939A, JP2007211243A2 and JP2007197574A2. Such non-conjugated polymers used as fluorescent light-emitting materials are disclosed in the patent applications JP2005108556, JP2005285661, and JP2003338375. In addition, the non-conjugated polymer may also be a polymer, with the conjugated functional units on the backbone linked by non-conjugated linking units. Examples of such polymers are disclosed in DE102009023154.4 and DE102009023156.0. The above patent documents are specially incorporated herein by reference in their entirety.

In a preferred embodiment, the mixture according to the present disclosure contains a compound according to the present disclosure and a triplet host.

The present disclosure further relates to a formulation comprising the organic compound or the mixture as described above, and at least one organic solvent. The present disclosure further provides a film prepared in a solution and containing the compound according to the present disclosure.

Examples of the organic solvents include, but are not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or their combinations.

In a preferred embodiment, the formulation according to the present disclosure is a solution.

In another preferred embodiment, the formulation according to the present disclosure is a suspension.

The formulation in the examples of the present disclosure may comprise an organic compound or its mixture from 0.01 to 20 wt %, more preferably from 0.1 to 15 wt %, more preferably from 0.2 to 10 wt %, and most preferably from 0.25 to 5 wt %.

The present disclosure also provides the use of said formulation as a coating or printing ink in the preparation of organic electronic devices, and particularly preferably by means of printing or coating in a preparation process.

Among them, suitable printing or coating techniques may include, but are not limited to, ink-jet printing, typography, screen printing, dip coating, spin coating, blade coating, roll printing, torsion printing, lithography, flexography, rotary printing, spray coating, brush coating or pad printing, slit type extrusion coating, and so on. Preferred are gravure printing, screen printing and inkjet printing. The solution or suspension may additionally comprise one or more components such as surface active compounds, lubricants, wetting agents, dispersing agents, hydrophobic agents, binders, etc., for adjusting viscosity, film forming properties, improving adhesion, and the like. For more information about printing techniques and their requirements for solutions, such as solvent, concentration, viscosity, etc., see Handbook of Print Media: Technologies and Production Methods, edited by Helmut Kipphan, ISBN 3-540-67326-1.

Based on the above organic compound, the present disclosure also provides the application of the organic compound as described above to an organic electronic device, which is selected from, but not limited to, organic light emitting diodes (OLED), organic photovoltaics (OPVs), organic light emitting electrochemical cells (OLEEC), organic field effect transistor (OFET), organic light emitting field effectors, organic lasers, organic spintronic devices, organic sensors, and organic plasmon emitting diodes, especially OLED. In the embodiments of the present disclosure, the organic compound is preferably used in the light-emitting layer of the OLED device.

The present disclosure further provides an organic electronic device which may comprise at least one polymer as described above. Typically, such an organic electronic device comprises at least a cathode, an anode, and a functional layer between the cathode and the anode, wherein the functional layer comprises at least one of the organic compounds as described above. The organic electronic device is selected from, but not limited to, organic light emitting diodes (OLED), organic photovoltaics (OPVs), organic light emitting electrochemical cells (OLEEC), organic field effect transistor (OFET), organic light emitting field effectors, organic lasers, organic spintronic devices, organic sensors, and organic plasmon emitting diodes In a particularly preferred embodiment, the above-described organic electronic device is OLED, which may include a substrate, an anode, at least one light-emitting layer, and a cathode.

The substrate may be opaque or transparent. Transparent substrates may be used to make transparent light-emitting components. See, for example, Bulovic et al., Nature 1996, 380, p29, and Gu et al., Appl. Phys. Lett. 1996, 68, p2606. The substrate may be rigid or flexible. The substrate may be plastic, metal, semiconductor wafer or glass. Most preferably the substrate has a smooth surface. Substrates free of surface defects are particularly desirable. In a preferred embodiment, the substrate is flexible and is selected from polymer films or plastic, with a glass transition temperature (Tg) of 150° C. or above, more preferably above 200° C., more preferably above 250° C., and most preferably above 300° C. Examples of suitable flexible substrates are poly (ethylene terephthalate) (PET) and polyethylene glycol (2,6-naphthalene) (PEN).

The anode may comprise a conductive metal or a metal oxide, or a conductive polymer. The anode may easily inject holes into the hole-injection layer (HIL) or the hole-transport layer (HTL) or the light-emitting layer. In one embodiment, the absolute value of the difference between the work function of the anode and the HOMO energy level or the valence band energy level of the emitter in the light-emitting layer or of the p-type semiconductor material of the HIL or HTL or the electron-blocking layer (EBL) is smaller than 0.5 eV, more preferably smaller than 0.3 eV, and most preferably smaller than 0.2 eV. Examples of anode materials include, but are not limited to, Al, Cu, Au, Ag, Mg, Fe, Co, Ni, Mn, Pd, Pt, ITO, aluminum-doped zinc oxide (AZO), and the like. Other suitable anode materials are known and may be readily selected for use by one of ordinary skill in the art. The anode material may be deposited using any suitable technique, such as suitable physical vapor deposition, including RF magnetron sputtering, vacuum thermal evaporation, electron beam (e-beam), and the like. In some embodiments, the anode is patterned. The patterned ITO conductive substrate is commercially available and may be used to fabricate the device according to the disclosure.

The cathode may comprise a conductive metal or a metal oxide. The cathode may easily inject electrons into the EIL or ETL or directly into the light-emitting layer. In one embodiment, the absolute value of the difference between the work function of the cathode and the LUMO energy level or the valence band energy level of the emitter in the light-emitting layer or of the n-type semiconductor material of the electron-injection layer (EIL) or the electron-transport layer (ETL) or the hole-blocking layer (HBL) is smaller than 0.5 eV, more preferably smaller than 0.3 eV, and most preferably smaller than 0.2 eV. In principle, all of the material that may be used as the cathode of an OLED may serve as a cathode material for the device of the present disclosure. Examples of the cathode material may include, but are not limited to, Al, Au, Ag, Ca, Ba, Mg, LiF/Al, MgAg alloys, BaF2/Al, Cu, Fe, Co, Ni, Mn, Pd, Pt, ITO. The cathode material may be deposited using any suitable technique, such as suitable physical vapor deposition, including RF magnetron sputtering, vacuum thermal evaporation, electron beam (e-beam), and the like.

OLEDs may also comprise other functional layers such as hole-injection layer (HIL), hole-transport layer (HTL), electron-blocking layer (EBL), electron-injection layer (EIL), electron-transport layer (ETL), and hole-blocking layer (HBL). Materials suitable for use in these functional layers are described in detail above.

In a preferred embodiment, in the light emitting device according to the present disclosure, the light-emitting layer thereof is prepared by printing with the formulation containing the compound of the present disclosure.

The light emitting device according to the present disclosure may have a light emission wavelength between 300 and 1000 nm, preferably between 350 and 900 nm, and more preferably between 400 and 800 nm.

The present disclosure also relates to the use of the organic electronic device according to the present disclosure in a variety of electronic devices including, but not limited to, display devices, lighting devices, light sources, sensors, and the like.

The disclosure will now be described with reference to the preferred embodiments, but the disclosure is not to be construed as being limited to the following examples. It is to be understood that the appended claims are intended to cover the scope of the disclosure. Those skilled in the art will understand that modifications can be made to various embodiments of the disclosure with the teaching of the present disclosure, which will be covered by the spirit and scope of the claims of the disclosure.

Specific examples of the deuterated organic compounds provided by the present disclosure are as follows:

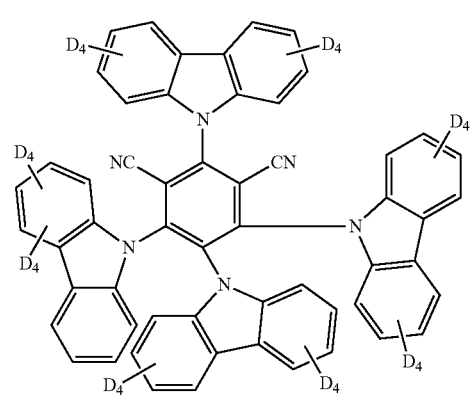

DEU1

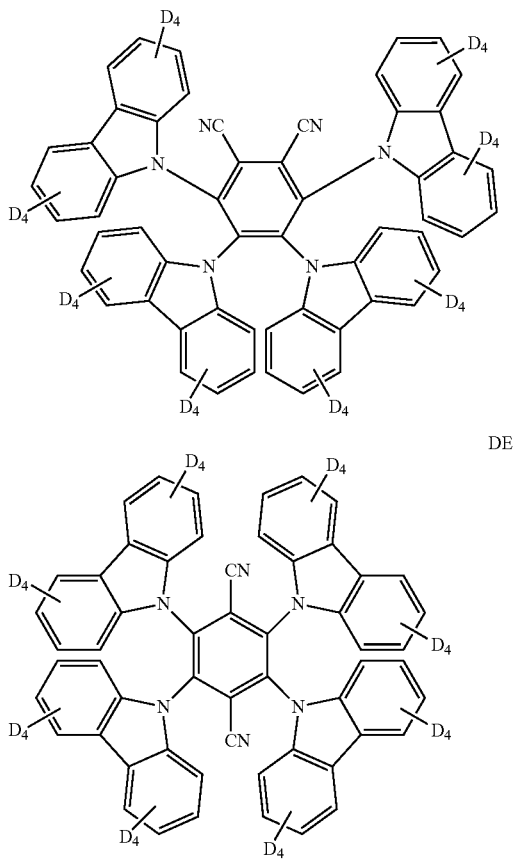

DEU3

In the above deuterated compounds DEU1, DEU2 and DEU3, D4 represents that there are four deuteriums in the benzene ring, wherein the synthesis route for the compound DEU1 is as follows:

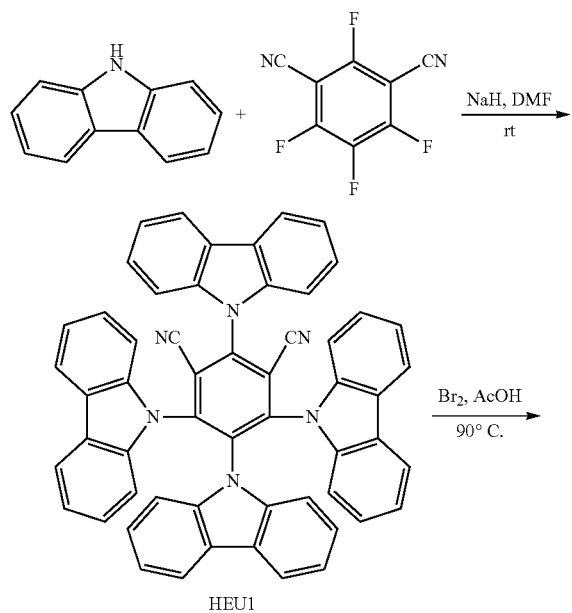

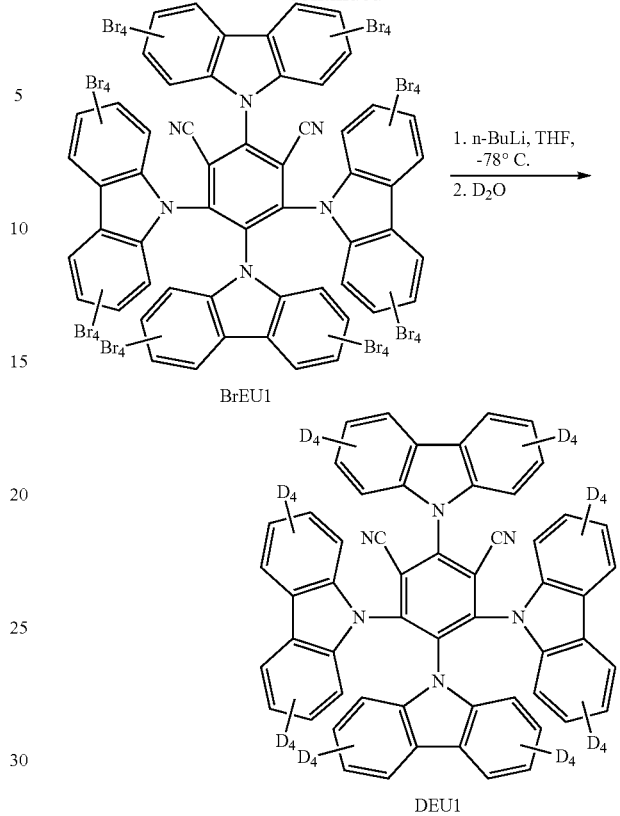

DEU1

The specific reaction steps are:

A. 40 mmol of carbazole and 10 mmol of 1,3,4,5-tetrafluoro-2,6-dicyanobenzene were added in sequence into a 500 ml round-bottom flask under nitrogen protection and dissolved in 300 ml of DMF solvent, and then 50 mmol of NaH powder was added in batches at room temperature. After completion of the addition, the reaction was continued at room temperature for 4 hours. After completion of the reaction, the reaction was quenched by adding water, followed by suction filtration, rinsing, extraction with dichloromethane, and other steps in turn. Finally, the organic phase was combined, dried over anhydrous magnesium sulfate, filtered, and the organic solvent was evaporated under reduced pressure to give a yellow crude product, which was recrystallized with dichloromethane and methanol to give 8 mmol of the product HEU1. The product was dried in vacuo dried in vacuo for later use. MS (APCI)=789.1;

b. 5 mmol of HEU1 resulted from the above step was dissolved in 500 ml of acetic acid solvent, heated to 90° C., and slowly added with 180 mmol liquid bromine dropwise. After completion of the dropwise addition, the reaction solution was heated to 120° C. and reacted for 12 hours. The reaction solution was cooled to room temperature and the remaining liquid bromide was removed by adding $Na_2S_2O_3$ aqueous solution. 4.8 mmol of light red solid powder BrEU1 was obtained by filtration; the resulted solid product was washed with ethanol and then the resulted product was dried in vacuo dried in vacuo for later use; and c. 4 mmol of BrEU1 was dissolved in 400 ml of anhydrous THF under the protection of nitrogen, cooled to −78° C., and added dropwise with 140 mmol of n-butyllithium. After completion of the addition of n-butyllithium, the reaction was continued at −78° C. for 30 minutes and the reaction solution was added dropwise with 140 mmol heavy water, gradually heated to room temperature, extracted with dichloromethane, and washed with water. The organic phase was combined, dried over anhydrous magnesium sulfate. The organic solvent was evaporated under reduced pressure to give a yellow crude product, which was recrystallized with dichloromethane and methanol to give 13.9 mmol of the product DEU. The product was dried in vacuo. MS(APCI)=821.4.

The synthesis steps of the compounds DEU2 and DEU3 were similar to those of DEU1, except that the starting materials used in the first synthesis step were 1,2,3,4-tetrafluoro-5,6-dicyanobenzene and 1,2,4,5-tetrafluoro-3,6-dicyanobenzene. All of the compounds DEU1, DEU2 and DEU3 were finally purified by sublimation.

The compounds to be compared with the deuterated compounds described above are corresponding non-predeuterated compounds labeled as Comp1, Comp2, and Comp3:

Comp1

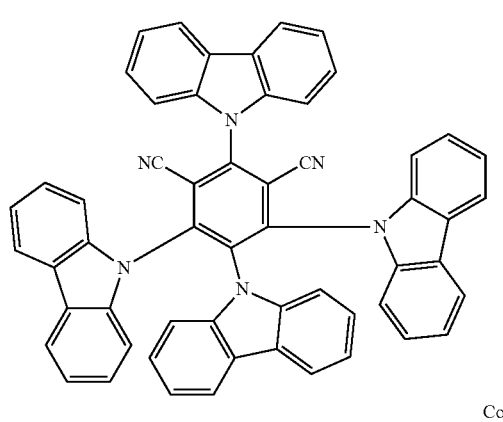

Comp2

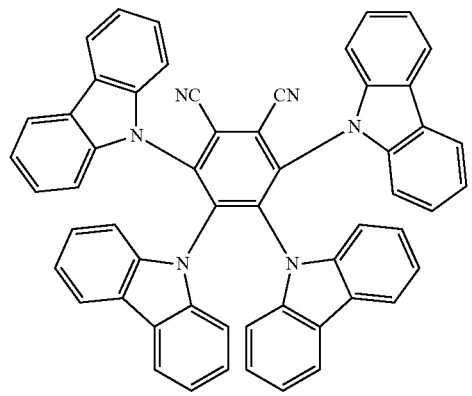

Comp3

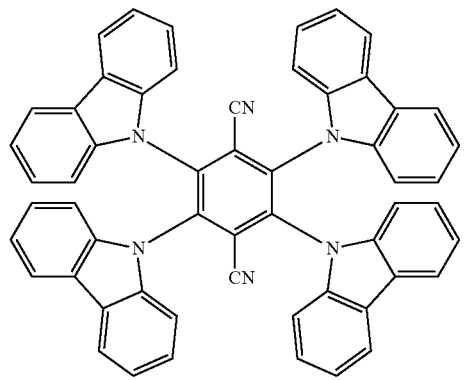

Preparation of OLED Devices:

The preparation steps of OLED devices having ITO/NPD (35 nm)/5% DEUx:CBP (15 nm)/TPBi (65 nm)/LiF (1 nm)/Al (150 nm)/cathode were as follows:

a. cleaning of a conductive glass substrate: before used for the first time, a variety of solvents might be used for cleaning, such as chloroform, ketone, isopropyl alcohol, and then UV ozone plasma treatment was carried out;

b. TL (35 nm), EML (15 nm), ETL (65 nm): thermal evaporation deposition in high vacuum ($1 \times 10^{-6}$ mbar, mbar);

c. cathode: thermal evaporation deposition in high vacuum ($1 \times 10^{-6}$ mbar) with LiF/Al (1 nm/150 nm); and d. packaging: packaging the device with UV curing resin in the nitrogen glove box.

The current-voltage (J-V) characteristics of OLEDs were characterized by characterization equipment, while important parameters such as efficiency, life and external quantum efficiency were recorded. The life of each device was as shown in Table 1, and it can be seen from the recorded data that: the life of OLED1 (corresponding to raw material DEU1), OLED2 (corresponding to raw material DEU1), and OLED3 (corresponding to raw material DEU1) were 1.5 times or above over that of RefOLED1 (corresponding to raw material Comp1), RefOLED2 (corresponding to raw material Comp2), and RefOLED3 (corresponding to raw material Comp3), respectively.

| Device | Emitter materials | Life hrs @ 200 nits |
|---|---|---|
| OLED1 | DEU1 | 1003 |
| OLED2 | DEU2 | 1423 |
| OLED3 | DEU3 | 1632 |
| RefOLED1 | Comp1 | 650 |
| RefOLED2 | Comp2 | 780 |
| RefOLED3 | Comp3 | 814 |

It is to be understood that the application of the present disclosure is not limited to the above-described examples and that a person skilled in the art may make improvement or modification in accordance with the above description, all of which are within the scope of the claims appended hereto.

What is claimed is:

1. An organic compound having the following structural formula (I):

wherein Ar is an aromatic or heteroaromatic structural unit, n and m are each an integer between 1 and 6, D is an electron donor group, wherein when m>1, each D is independently selected from the same or different electron donor groups, A is an electron acceptor group, wherein when n>1, each A is independently selected from the same or different electron acceptor groups, wherein for the organic compound, (S1−T1)≤0.35 eV and at least one H atom of the organic compound is substituted by deuterium, and wherein (S1−T1) refers to a difference between singlet energy level (S1) and triplet energy level (T1).

2. The organic compound according to claim 1, wherein (S1−T1)≤0.25 eV.

3. The organic compound according to claim 1, wherein at least one H atom in at least one electron donor group D is substituted by deuterium.

4. The organic compound according to claim 1, wherein at least one H atom in at least one electron acceptor group A is substituted by deuterium.

5. The organic compound according to claim 1, wherein at least one H atom in Ar is substituted by deuterium.

6. The organic compound according to claim 1, wherein the electron donor group D comprises any of the following groups:

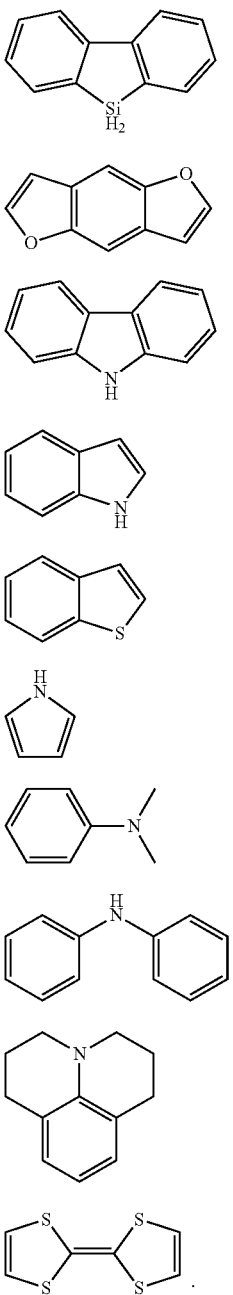

D1

D2

D3

D4

D5

D6

D7

D8

D9

D10

7. The organic compound according to claim 1, wherein the electron acceptor group A is selected from F, cyano, and groups comprising any of the following:

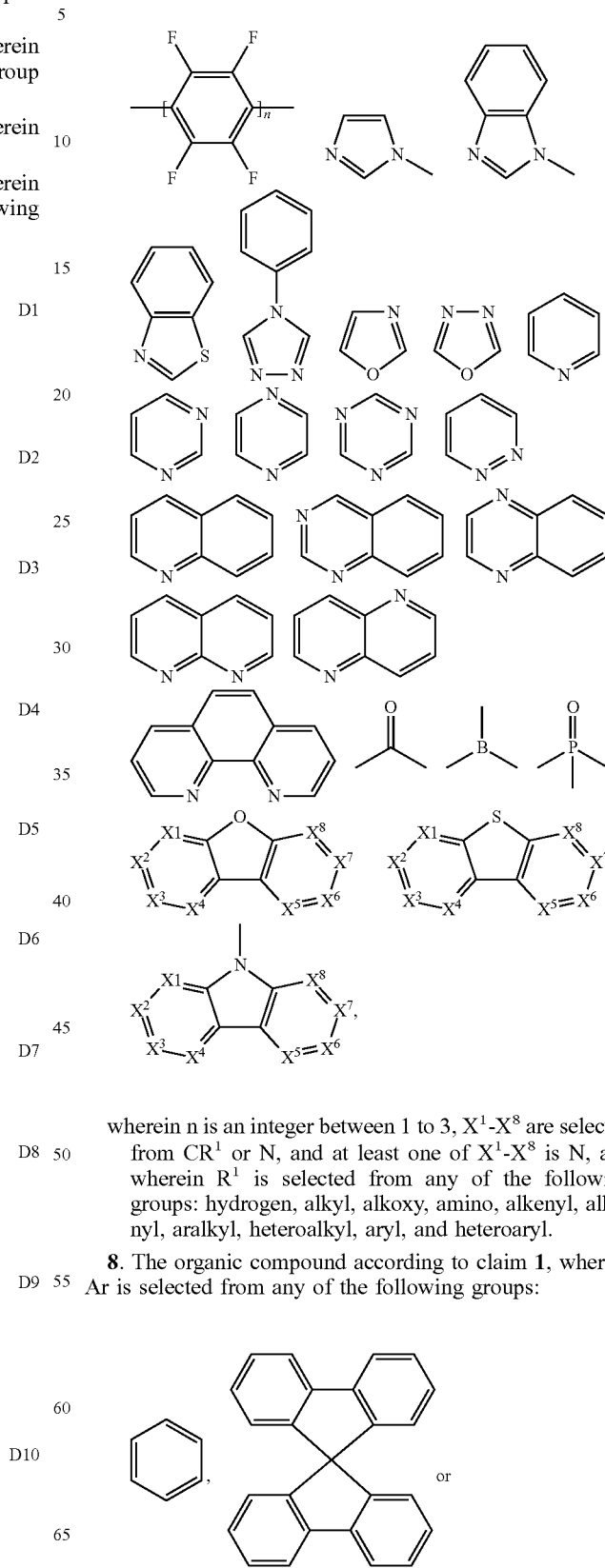

wherein n is an integer between 1 to 3, $X^1$-$X^8$ are selected from $CR^1$ or N, and at least one of $X^1$-$X^8$ is N, and wherein $R^1$ is selected from any of the following groups: hydrogen, alkyl, alkoxy, amino, alkenyl, alkynyl, aralkyl, heteroalkyl, aryl, and heteroaryl.

8. The organic compound according to claim 1, wherein Ar is selected from any of the following groups:

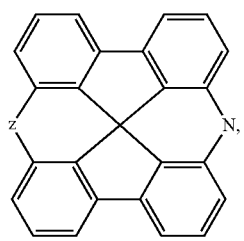
wherein z is O or S.
9. The organic compound according to claim 1, wherein more than 20% of the H atoms are substituted by deuterium.
10. The organic compound according to claim 1, selected from the table listed below, wherein one or more H are substituted by deuterium:
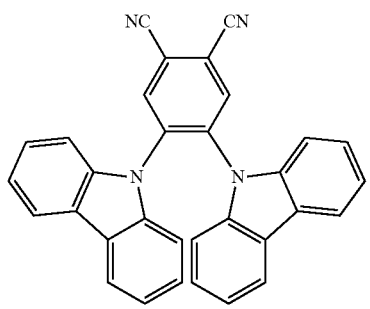
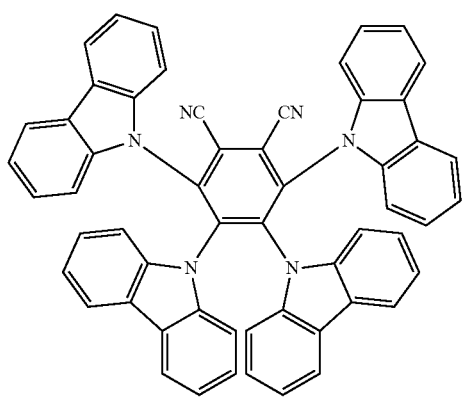
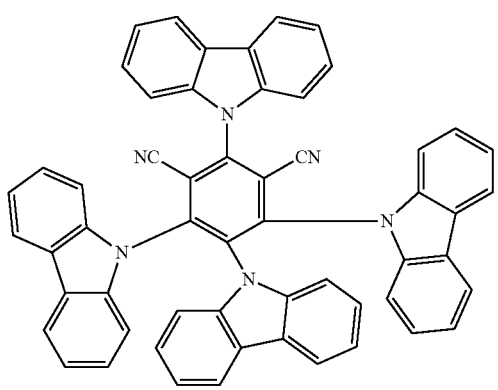
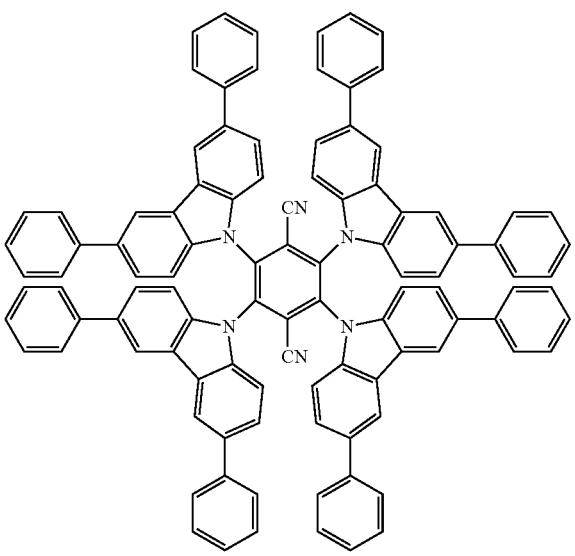
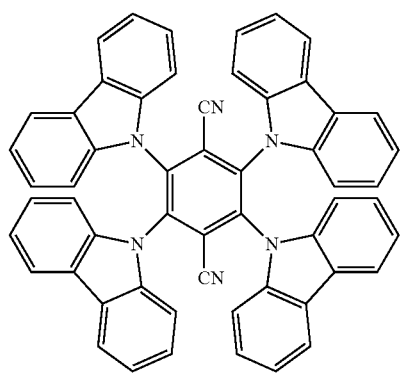
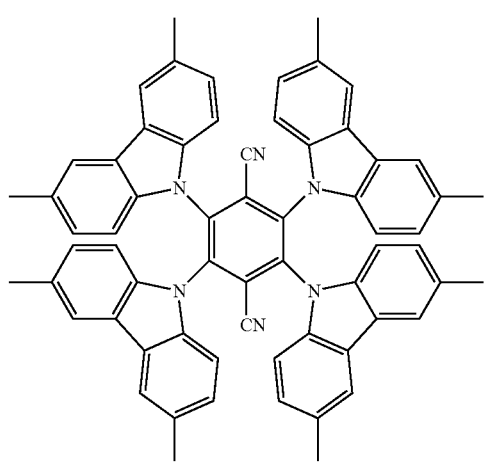

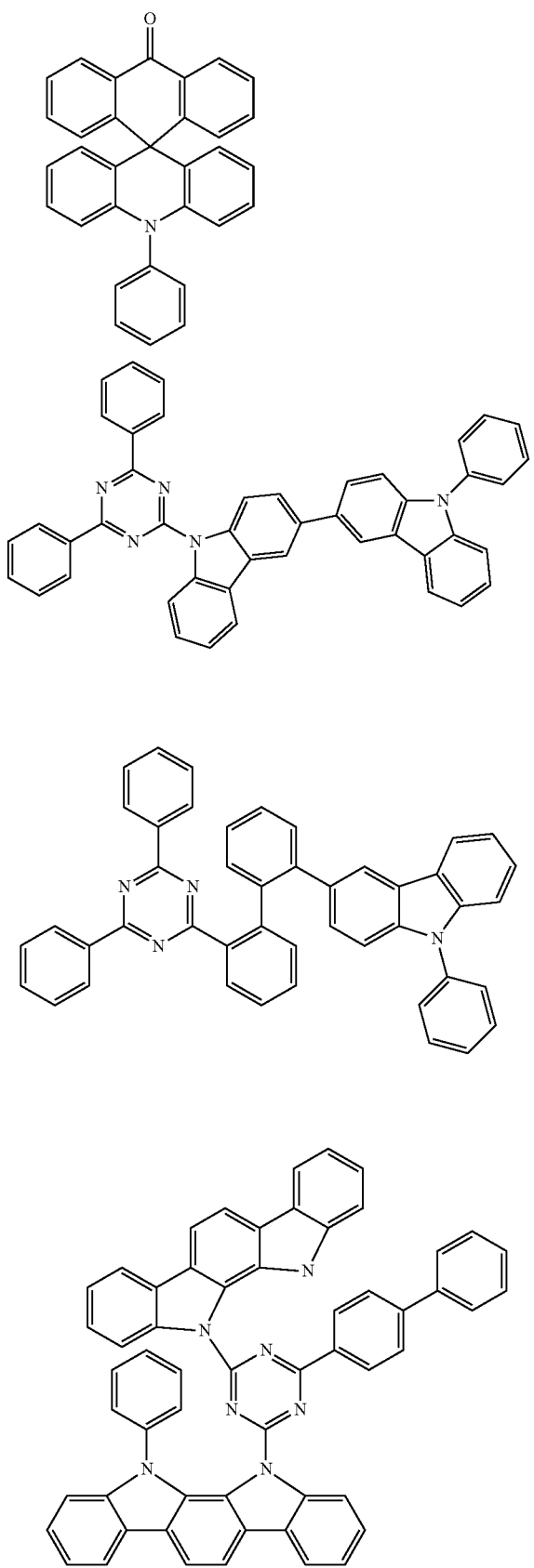
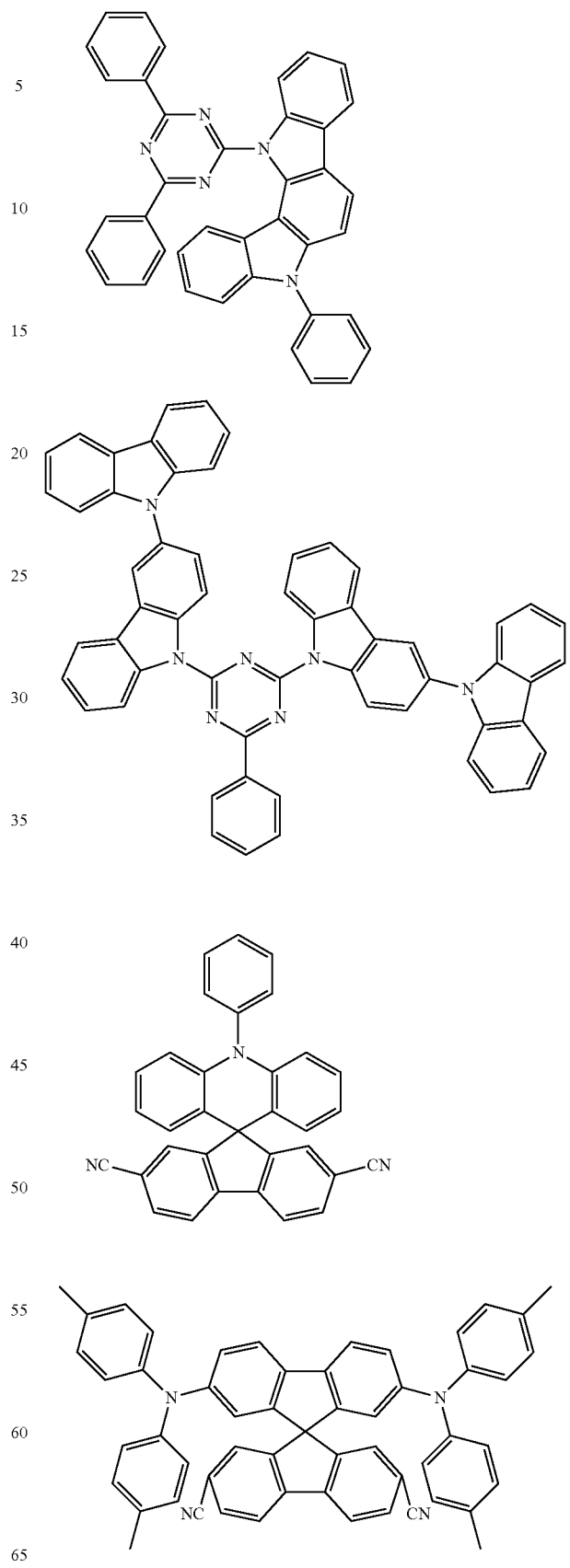

-continued

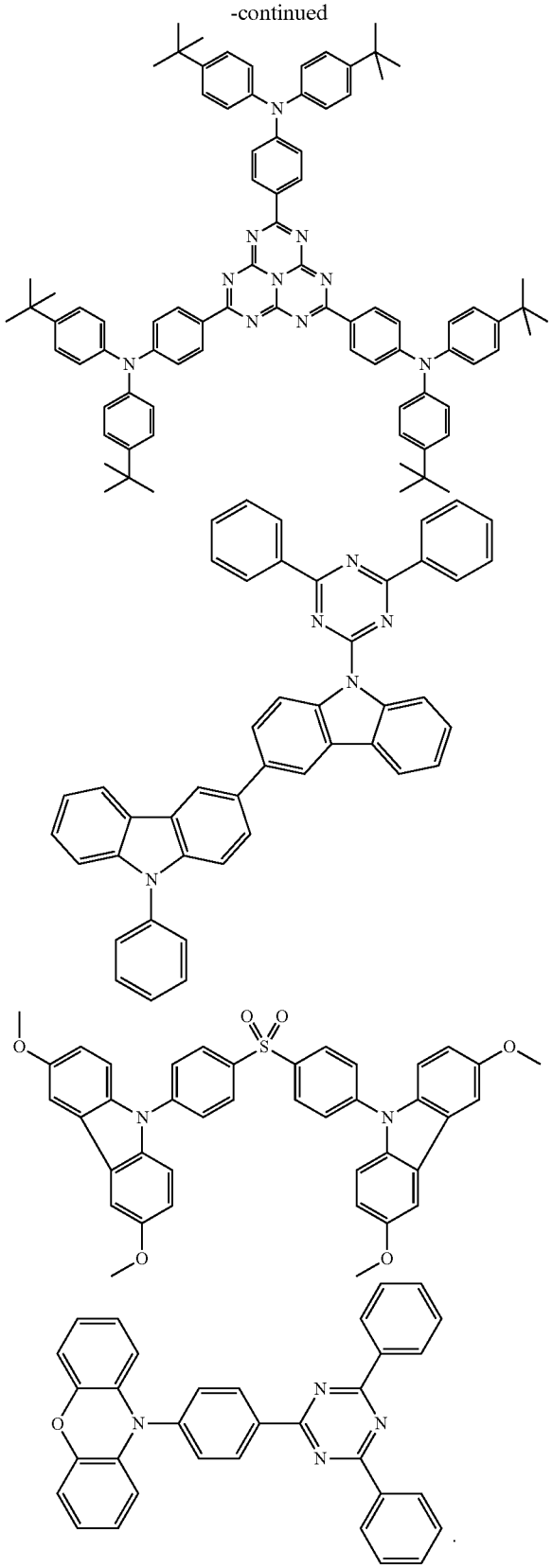

11. A mixture comprising at least one organic compound according to claim 1 and further an organic functional material selected from a hole-injection or hole-transport material, a hole-blocking material, an electron-injection or electron-transport material, an electron-blocking material, an organic host material, a singlet emitter, and a triplet emitter.

12. A formulation comprising an organic compound having the following structural formula (I):

$$(A)_n\text{—}Ar\text{—}(D)_m \quad (I)$$

wherein Ar is an aromatic or heteroaromatic structural unit, n and m are each an integer between 1 and 6, D is an electron donor group, wherein when m>1, each D is independently selected from the same or different electron donor groups, A is an electron acceptor group, wherein when n>1, each A is independently selected from the same or different electron acceptor groups, wherein for the organic compound, (S1−T1)≤0.35 eV and at least one H atom of the organic compound is substituted by deuterium, and at least one organic solvent, and wherein (S1−T1) refers to a difference between singlet energy level (S1) and triplet energy level (T1).

13. The formulation according to claim 12, wherein the organic solvent selecting from methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or a mixture thereof.

14. The formulation according to claim 13, wherein the formulation includes the organic compound with a weight percentage from 0.01 to 20%.

15. The formulation according to claim 13, wherein the formulation includes the organic compound with a weight percentage from 0.1 to 15%.

16. The formulation according to claim 13, wherein the formulation includes the organic compound with a weight percentage from 0.2 to 10%.

17. The formulation according to claim 13, wherein the formulation includes the organic compound with a weight percentage from 0.25 to 5%.

* * * * *